US011857256B2

(12) United States Patent
Rice-Jones et al.

(10) Patent No.: US 11,857,256 B2
(45) Date of Patent: Jan. 2, 2024

(54) OPTICAL COHERENCE TOMOGRAPHY SCAN CONTROL

(71) Applicant: OPTOS PLC, Scotland (GB)

(72) Inventors: Jenny Rice-Jones, Dunfermline (GB); Gary Young, Dunfermline (GB); George McGaughay, Dunfermline (GB); Scott Dalzell, Dunfermline (GB); Laurie Ibbs, Dunfermline (GB); Geoff Smith, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 102 days.

(21) Appl. No.: 16/721,899

(22) Filed: Dec. 19, 2019

(65) Prior Publication Data

US 2020/0196854 A1 Jun. 25, 2020

(30) Foreign Application Priority Data

Dec. 20, 2018 (EP) .................................. 18214686

(51) Int. Cl.
*A61B 3/00* (2006.01)
*A61B 3/10* (2006.01)
(Continued)

(52) U.S. Cl.
CPC .......... *A61B 3/0033* (2013.01); *A61B 3/0025* (2013.01); *A61B 3/0041* (2013.01);
(Continued)

(58) Field of Classification Search
CPC ... A61B 3/0033; A61B 3/0025; A61B 3/0041; A61B 3/102; A61B 3/1225; A61B 3/103;
(Continued)

(56) References Cited

U.S. PATENT DOCUMENTS

2008/0100612 A1 5/2008 Dastmalchi et al.
2009/0123044 A1 5/2009 Huang et al.
(Continued)

FOREIGN PATENT DOCUMENTS

JP 2011064978 A 1/2011
JP 2013165953 A 8/2013
(Continued)

OTHER PUBLICATIONS

Extended European Search Report from corresponding European Application No. 18214686.0, dated Jun. 4, 2019.
(Continued)

*Primary Examiner* — Angie Badawi
(74) *Attorney, Agent, or Firm* — FAEGRE DRINKER BIDDLE & REATH

(57) ABSTRACT

An apparatus, method, computer-readable medium, and computer program product, for designating an OCT scan location to be performed on a retina. The apparatus comprises a display device for displaying an image comprising a background image of the retina and a planning element designating the location; a touch-sensitive input device that generates touch interaction data indicative of touch interaction of a user with the input device; an image manipulation module determines, based on the touch interaction data, a manipulation to be performed on the displayed image, and applies the image manipulation to the image in response to each touch interaction to generate an updated image to display; and a scan location designation module generates data indicative of the location of the OCT scan to be performed, based on a location of the planning element on the background image in at least one updated image.

20 Claims, 11 Drawing Sheets

(51) Int. Cl.
  *A61B 3/12* (2006.01)
  *G06F 3/0354* (2013.01)
  *G06F 3/04845* (2022.01)
  *G06F 3/0485* (2022.01)
  *G06F 3/04883* (2022.01)

(52) U.S. Cl.
  CPC ............ *A61B 3/102* (2013.01); *A61B 3/1225* (2013.01); *G06F 3/03547* (2013.01); *G06F 3/0485* (2013.01); *G06F 3/04845* (2013.01); *G06F 3/04883* (2013.01); *G06F 2203/04808* (2013.01)

(58) Field of Classification Search
  CPC ............. G06F 3/03547; G06F 3/04845; G06F 3/0485; G06F 3/04883; G06F 2203/04808; G06F 2203/04806; G16H 40/63
  See application file for complete search history.

(56) References Cited

U.S. PATENT DOCUMENTS

| | | | |
|---|---|---|---|
| 2010/0293500 A1 | 11/2010 | Cragun et al. | |
| 2012/0182373 A1 | 7/2012 | Yoshinori | |
| 2013/0188135 A1 | 7/2013 | Iwase et al. | |
| 2013/0258283 A1 | 10/2013 | Goto et al. | |
| 2014/0164913 A1* | 6/2014 | Jaros | G06F 16/9577 715/243 |
| 2014/0211162 A1* | 7/2014 | Matsuoka | A61B 3/0025 351/208 |
| 2014/0276057 A1 | 9/2014 | Lee et al. | |
| 2016/0026375 A1* | 1/2016 | Wu | G06F 3/0481 715/765 |
| 2016/0027201 A1* | 1/2016 | Saito | G06T 13/80 345/475 |
| 2016/0213246 A1 | 7/2016 | Muto et al. | |
| 2017/0018077 A1 | 1/2017 | Iwase et al. | |
| 2017/0100030 A1* | 4/2017 | Bedworth | A61B 3/0033 |
| 2017/0228521 A1 | 8/2017 | Appakaya et al. | |
| 2018/0273050 A1* | 9/2018 | Tertoolen | G08G 1/096861 |
| 2019/0286305 A1* | 9/2019 | Sevenster | G06F 40/169 |

FOREIGN PATENT DOCUMENTS

| | | |
|---|---|---|
| JP | 2013212176 A | 10/2013 |
| JP | 2014147495 A | 8/2014 |
| JP | 2015160105 A | 9/2015 |
| JP | 2016101298 A | 6/2016 |
| JP | 2017056280 A | 3/2017 |
| JP | 2018000246 A | 1/2018 |

OTHER PUBLICATIONS

Notice of Reason for Rejection dated Apr. 8, 2021, in Japanese Patent Application No. 2019-230610 (With English Translation Attached).

* cited by examiner

OPTICAL COHERENCE TOMOGRAPHY SCAN CONTROL

FIELD

Example aspects herein generally relate to the field of optical coherence tomography (OCT) and, more particularly, to the designation of a location of an OCT scan to be performed on a retina of an eye.

BACKGROUND

Optical coherence tomography is a well-known interferometric imaging technique which is widely used in ophthalmology as a power diagnostic tool. Conventional approaches to setting up an OCT scan typically require an initial step of acquiring an image of a portion of the retina of an eye on which the OCT scan is to be performed. This image may be acquired using a scanning laser ophthalmoscope (SLO) or a fundus camera, for example. The user may then examine the retinal image and, where necessary, magnify a portion of interest to obtain a magnified view, and use a computer mouse or the like to designate a part of the magnified image that is be imaged by the OCT scanner.

SUMMARY

The present inventors have recognised that conventional approaches to designating the location of a retinal OCT scan of the kind identified above generally employ user interfaces which make it difficult for the user to explore the acquired image in an efficient and intuitive way, making the identification of pathologies that warrant further investigation using OCT, and therefore the designation of the intended OCT scan location, a time-consuming process. In particular, such conventional approaches lack the ability to pan the image and zoom in and out of it, as necessary, whilst being able to move and retain the intended location of the OCT scan during the course of these operations.

In view of these limitations, the present inventors have devised a computer program for designating a location of an OCT scan to be performed on a retina of an eye. The computer program comprises a display control software module which, when executed by a processor, causes the processor to generate, based on image data defining a background image of a portion of the retina and a foreground graphical planning element for designating a location on the retina of the OCT scan to be performed, display control signals for controlling a display device to display an image defined by the image data. The computer program further comprises an image manipulation software module which, when executed by the processor, causes the processor to receive respective touch interaction data indicative of at least one sequence of detected locations on a touch-sensitive surface of a touch-sensitive input device for each of a plurality of touch interactions of a user with the touch-sensitive surface, and to determine, based on each of the touch interaction data, a respective image manipulation to be performed on the image data that define the image being displayed by the display device. Each image manipulation comprises at least one of: a resizing of both the foreground graphical planning element and the background image by a common factor; a translation of the foreground graphical planning element relative to the background image; or a panning of the image being displayed. The image manipulation software module, when executed by the processor, further causes the processor to apply the determined image manipulation to the image data that define the image being displayed by the display device, in response to each of the touch interactions, so as to generate a respective updated image data defining an updated image that is to be displayed on the display device, and to cause the display control software module to generate, based on the updated image data generated in response to each of the touch interactions, respective display control signals for controlling the display device to display an updated image defined by the updated image data. The computer program further comprises a scan location designation software module which, when executed by the processor causes the processor to generate OCT scan location data indicative of the location of the OCT scan that is to be performed on the retina based on a location of the foreground graphical planning element on the background image of the retina in at least one of the updated images.

The present inventors have further devised a non-transitory computer-readable storage medium storing the computer program set out above.

The present inventors have further devised a signal carrying the computer program set out above.

The present inventors have further devised an apparatus for designating a location of an OCT scan to be performed on a retina of an eye. The apparatus comprises a display device configured to display an image comprising a background image of a portion of the retina and a foreground graphical planning element for designating a location on the retina of the OCT scan to be performed. The apparatus also comprises a touch-sensitive input device having a touch-sensitive surface and configured to generate respective touch interaction data indicative of at least one sequence of detected locations for each of a plurality of touch interactions of a user with the touch-sensitive surface. The apparatus further comprises an image manipulation module configured to determine, based on each of the touch interaction data, a respective image manipulation to be performed on the image displayed by the display device, each image manipulation comprising at least one of: a resizing of both the foreground graphical planning element and the background image by a common factor; a translation of the foreground graphical planning element relative to the background image; or a panning of the image being displayed. The image manipulation module is further configured to apply the determined image manipulation to the image being displayed on the display device in response to each of the touch interactions so as to generate a respective updated image that is displayed on the display device. The apparatus further comprises a scan location designation module configured to generate OCT scan location data indicative of the location of the OCT scan that is to be performed on the retina based on a location of the foreground graphical planning element on the background image of the retina in at least one of the updated images.

BRIEF DESCRIPTION OF THE DRAWINGS

Embodiments of the invention will now be explained in detail, by way of non-limiting example only, with reference to the accompanying figures, described below. Like reference numerals appearing in different ones of the figures can denote identical or functionally similar elements, unless indicated otherwise.

DETAILED DESCRIPTION OF EMBODIMENTS

Figure 1:
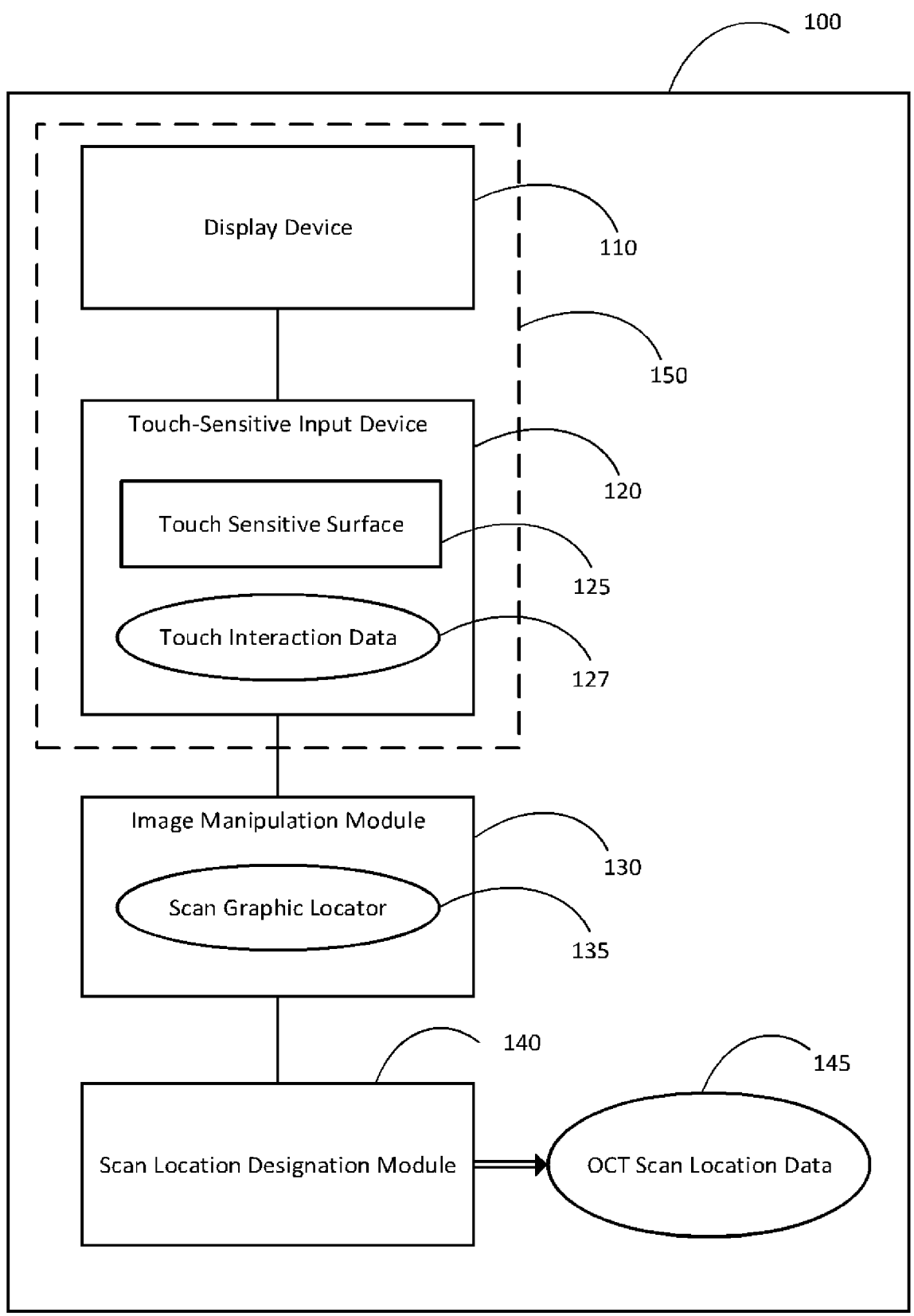
FIG. 1 is a schematic illustration of an apparatus for designating a location of a retinal OCT scan, according to a first example embodiment herein.

Example embodiments of the present invention will now be described in detail with reference to the accompanying drawings.

The phraseology and terminology used herein is for the purpose of description and should not be regarded as limiting. The use of "including," "comprising," "having" and variations thereof herein, is meant to encompass the items listed thereafter, equivalents thereof, and additional items, as well as alternate embodiments consisting of the items listed thereafter exclusively. In one example embodiment herein, the systems, apparatuses, methods, computer-readable mediums, and computer programs described herein consist of one, each combination of more than one, or all of the described elements, acts, or components.

Any references to embodiments or elements or acts of the systems, apparatuses, methods, computer-readable mediums, and computer programs herein referred to in the singular may also embrace embodiments including a plurality of these elements, and any references in plural to any embodiment or element or act herein may also embrace embodiments including only a single element. References in the singular or plural form are not intended to limit the presently disclosed systems, apparatuses, methods, computer-readable mediums, and computer programs, their components, acts, or elements to single or plural configurations. References to any act or element being based on any information, act or element may include embodiments where the act or element is based at least in part on any information, act, or element.

Any embodiment disclosed herein may be combined with any other embodiment, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. Such terms as used herein are not necessarily all referring to the same embodiment. Any embodiment may be combined with any other embodiment, inclusively or exclusively, in any manner consistent with the aspects and embodiments disclosed herein.

References to "or" may be construed as inclusive so that any terms described using "or" may indicate any of a single, more than one, and all of the described terms.

Where technical features in the drawings, detailed description or any claim are followed by reference signs, the reference signs have been included for the sole purpose of increasing the intelligibility of the drawings, detailed description, and claims. Accordingly, neither the reference signs nor their absence have any limiting effect on the scope of any claim elements.

First Example Embodiment

FIG. 1 is a schematic illustration of an apparatus 100 according to a first example embodiment herein, for designating a location of an OCT scan to be performed by an OCT scanner (not shown) to image a portion of the retina of a subject's eye. The apparatus 100 may designate such a location on a surface of the retina by generating OCT scan location data 145 indicative of one or more control parameter values of the OCT scanner for controlling the OCT scanner such that its scan covers a particular region of the retina. The one or more control parameter values of the OCT scanner may, for example, correspond to an angular displacement of one or more beam-scanning mirrors (not shown) of the OCT scanner that define, e.g., a point on the retina where the OCT scan is to be performed, or a point on the retina serving as a reference point for setting the location of the OCT scan (e.g., a point on which the OCT scan is to be centred). In this regard, it should be noted that the OCT scan to be performed by the OCT scanner may be, by example and without limitation, an A-scan (in which two or more OCT measurements are performed at different points in a depth direction of the retina, all for a common location on the surface of the retina), a B-scan (in which two or more A-scans are performed, each at a different coordinate value taken along a first direction (e.g., a direction along an x-axis) on the surface of the retina) or a C-scan (in which two or more B-scans are performed, each at a different coordinate value taken along a second, different direction (e.g., an orthogonal, y-axis direction) on the surface of the retina).

As illustrated in FIG. 1, the apparatus 100 comprises a display device 110, a touch-sensitive input device 120, an image manipulation module 130 and a scan location designation module 140.

Figure 2:
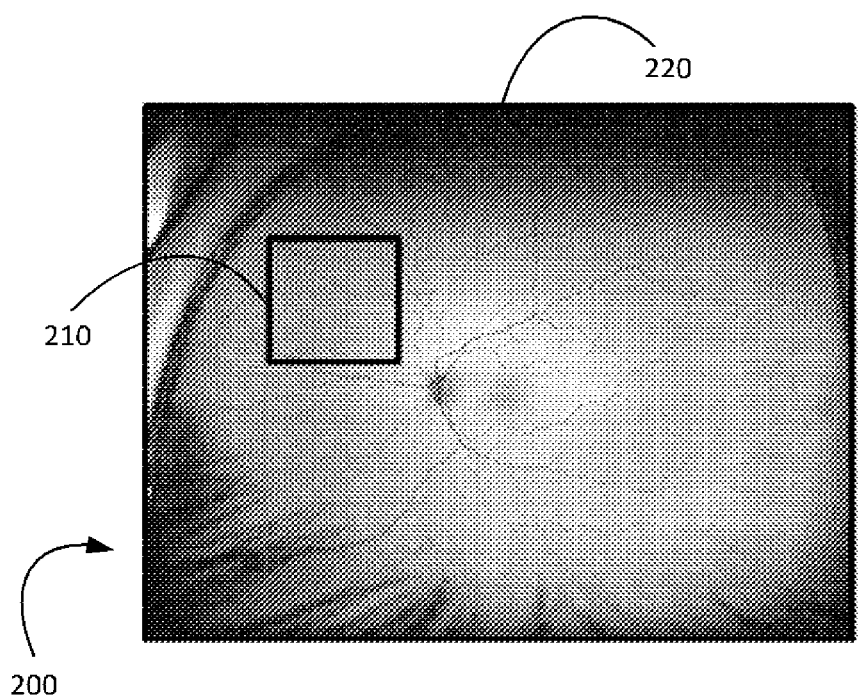
FIG. 2 is an illustrative image comprising a background image 220 of a portion of a retina and a foreground graphical planning element 210 superimposed on the background image 220, according to an example aspect herein.

The display device 110 is configured to display an image 200, as shown in FIG. 2, for example, comprising a number of elements including a background image 220 of at least a portion of the retina and a foreground graphical planning element 210 that is superimposed on the background image 220, for designating a location on the retina of the OCT scan that is to be performed. The display device 110 may, as in the present embodiment, form part of a touch-screen device 150, which integrates the functionalities of the display device 110 and the touch-sensitive input device 120. Thus, the display device 110 and the touch-sensitive input device 120 may be an integrally formed user input/output interface that forms the touch-screen device 150. Alternatively, the display device 110 may be an LCD screen or any other type of visual display unit (VDU), and/or may be separate from the device 120. The background image 220 may be obtained in a manner as will be described further below.

Figure 3A:
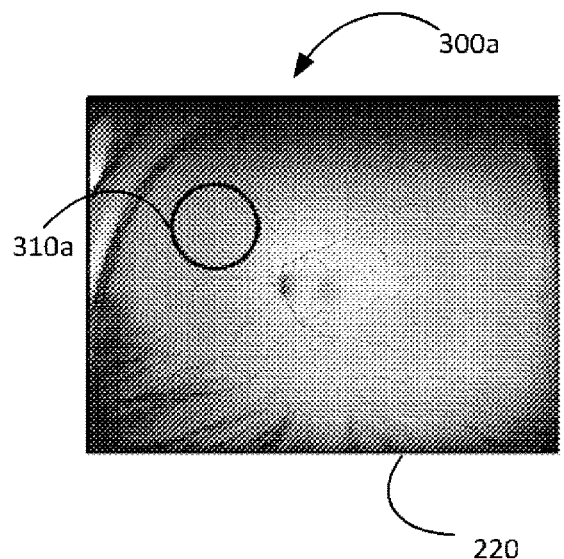
FIGS. 3(*a*) to 3(*d*) are variants of the image shown in FIG. 2, each including a different foreground graphical planning element, according to an example aspect herein.
Figure 3B:
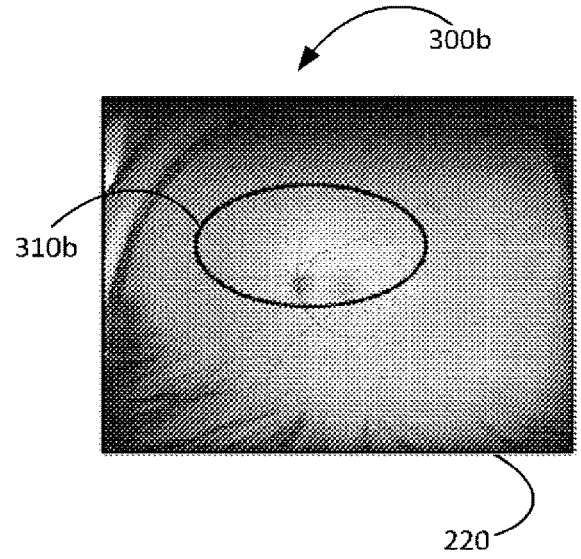

The foreground graphical planning element 210 may, as in the illustrated embodiment, have a rectangular shape, as shown in FIG. 2. As a further alternative, the foreground graphical planning element 210 may define a two-dimensional region whose boundary is not rectangular but may take any other predetermined shape suitable for designating a two-dimensional region of the retina for performing a C-scan, such as a circle or an ellipse, for example and without limitation. FIG. 3(a) shows an alternative example of the image, labelled 300a, comprising the background image 220 and a circular foreground graphical planning element 310a, while FIG. 3(b) shows another example of the image, labelled 300b, comprising the background image 220 and an elliptical foreground graphical planning element 310b.

Figure 3C:
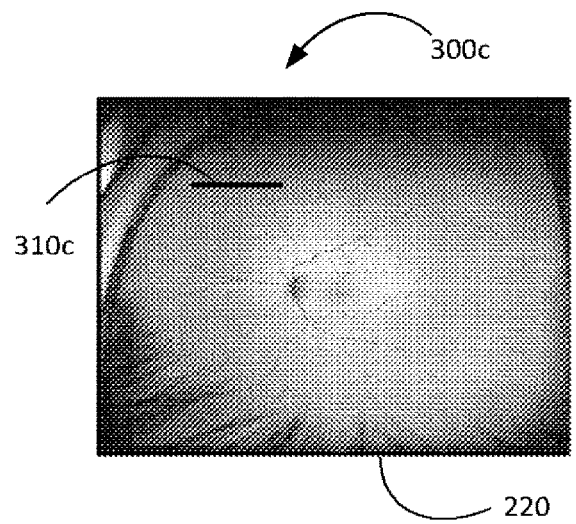
Figure 3D:
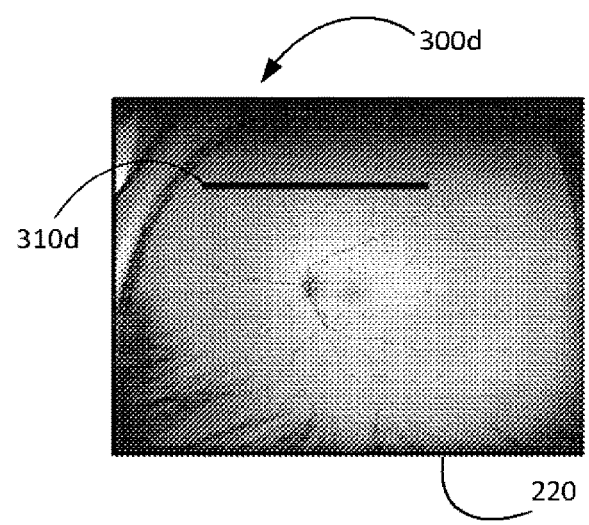

Moreover, the foreground graphical planning element 210 need not define a two-dimensional region on the background image 220 and may alternatively take the form of a point superimposed on the background image 220 (for designating the location of an A-scan) or a line segment superimposed on the background image 220 (for designating the location of an B-scan). FIGS. 3(c) and 3(d) show alternative examples of the image, comprising the background image 220 and foreground graphical planning element, labelled 310c and 310d, respectively, in the form of line segments of different lengths.

The foreground graphical planning element 210 may provide a proportionate representation of a region of the retina to be captured in the OCT scan. However, it should be noted that the shape of the foreground graphical planning element 210 need not in general be indicative of the shape of the region of the retina to be covered by the OCT scan. For example, the foreground graphical planning element 210 may take the form of a point whose location on the background image 220 is understood to have a predefined positional relationship to the (one- or two-dimensional) region of the retina on the background image 220 that is to be covered by the scan. By example, the point could serve to designate a centre of a one- or two-dimensional region to be scanned, an end of a one-dimensional region to be scanned, a corner of a two-dimensional region to be scanned, or the like. The location of the foreground graphical planning element 210 on the background image 220 in the coordinate space in which each extends is defined by a scan graphic locator, comprising coordinates of a predefined portion of the foreground graphical planning element 210 (e.g., the centre of a rectangular foreground graphical planning element 210) in an image pixel coordinate system of the background image 220, for example. The location of the foreground graphical planning element 210 on the background image 220 is set by the values of the scan graphic locator.

In some example embodiments herein, the foreground graphical planning element 210 has a shape that is manipulable/changeable. By example, in those embodiments the foreground planning element 210 may be controlled to select any of the foregoing or other shapes for the element 210, such that the element 210 takes on the selected shape(s), when selected. Also, one or more of the shapes may be, for example, at least one point, line segment, a two-dimensional shape, or a three-dimensional shape. Also in one example embodiment herein, the foreground graphical planning element 210 can be controlled to expand or reduce its size, and/or to deform at least part thereof. Each of the foregoing functionalities can be performed via a user interface, such as, by example and without limitation, touch-sensitive input device 120.

The background image 220 may, as in the present embodiment, be produced by a scanning imaging system (not shown), such as, for example, an ultra-wide-field scanning laser ophthalmoscope (UWF-SLO) capable of generating an ultra-wide field image of up to 80% of the retinal surface. Alternatively, the background image 220 may be produced by other types of scanning imaging systems, such as, for example, a scanning laser ophthalmoscope (SLO), a combined SLO-OCT scanner, a fundus camera or any other suitable type of retinal imaging system. The background image 220 may be a Red-Green (RG) reflectance image or an image from other fluorescence modes, or any other suitable type of image.

The apparatus 100 may acquire the background image 220 of a portion of the retina by any suitable means known to those versed in the art. For example, the apparatus 100 may receive the background image 220 from a scanning imaging system (not shown) via a direct communication link (which may be provided by any suitable wired or wireless connection, e.g. a Universal Serial Bus (USB) or a Bluetooth™ connection), an indirect communication link (which may be provided by a network comprising a Local Area Network (LAN), a Wide Area Network (WAN) and/or the Internet), or via a memory in which the background image 220 is stored, although these examples are not exclusive. Furthermore, the background image 220 may be acquired by the apparatus 100 (and may furthermore subsequently be processed to designate a location of an OCT scan to be performed on a retina of an eye, as described below) as the background image data is being generated by the scanning imaging system, i.e., the image data may be acquired "on the fly", without waiting for the scanning imaging system to finish generating all of the image data that forms the background image 220 of the at least a portion of the retina.

The touch-sensitive input device 120 has a touch-sensitive surface 125, with which the user may interact directly using one or more digits of their hand, or indirectly using an implement such as a stylus, for example. The touch-sensitive input device 120 is configured to generate respective touch interaction data 127 indicative of at least one sequence of detected locations for each of a plurality of touch interactions of the user with the touch-sensitive surface 125. In other words, the touch-sensitive input device 120 logs (for example, by recording) detected locations of one or more points of contact between, e.g., a finger of the user, a stylus held by the user or the like and the touch-sensitive surface 125 during the course of a touch interaction between the user and the touch-sensitive input device 120, such that the detected locations are recorded in the sequence (order) in which they were detected. The ordering of the detected locations may be recorded using timestamps assigned to the detected locations, by sequential numbering of the detected locations, or in any other suitable manner.

For example, where the touch interaction takes the form of a single-touch drag (where the user touches the touchscreen with a finger (or a tool such a stylus) and then drags the finger (or tool, as the case may be) across its surface while drawing a line or a curve or any other shape/pattern on the touch-sensitive surface 125), for example, the touch-sensitive input device 120 logs detected locations of the point of contact between the user's finger (or the tool) and the touch-sensitive surface 125 of the touch-sensitive input device 120 during the course of the single-touch drag, as a single sequence of detected locations. The touch-sensitive input device 120 may determine that the sequence of detected locations relates to a single-touch drag if the number of locations in the sequence exceeds a predetermined threshold number (for example, the number of locations may correspond to 20 pixels) or where the duration of the touch interaction corresponding to the sequence of detected locations exceeds a predetermined threshold duration (e.g. 300 ms), for example. The predetermined threshold number or the predetermined threshold duration (as the case may be) may be configurable and could be adjusted by trial and error, for example, to optimise the performance of the touch-sensitive input device 120.

Where the touch interaction is a double-tap of at least one finger of the user (or the stylus or other tool for interacting with the touch-sensitive input device 120, as the case may be) on the touch-sensitive surface 125, the touch-sensitive input device 120 may determine that the touch interaction is a double-tap by determining that the durations of the two interactions constituting the double-tap are both below respective threshold values (which may be the same value as (or a different value from), for example, the predetermined threshold value noted above that may be used to identify a touch interaction as a single-touch drag) and, optionally, that the interval between the end of the first interaction and the start of the second interaction is below a threshold value. Where the touch interaction is identified as a double-tap, the touch-sensitive input device 120 may log detected locations of the points of contact between the user's finger (or the tool) and the touch-sensitive surface 125 made during the course of the double-tap interaction, which will usually be the same or almost the same.

It should be noted that the touch-sensitive input device 120 may be configured to generate touch interaction data 127 indicative of more than one sequence of detected locations for some kinds of touch interaction of the user with the touch-sensitive surface 125. For example, in the case of a pinch interaction of the user with the touch-sensitive input device 120, where the user places a first and a second digit of their hand (often the thumb and forefinger) on the touch-sensitive surface 125 and moves those digits closer together ("pinching in") or further apart ("pinching out") while maintaining contact between each of the digits and the touch-sensitive surface 125, the touch-sensitive input device 120 logs detected locations of the respective points of contact between the first and second digits and the touch-sensitive surface 125 during the course of the pinch interaction, as a respective first and second sequence of detected locations. Since the locations of the points of contact are recorded as sequences, the touch-sensitive input device 120 is able to determine whether the user is moving their digits closer together or further apart, based on whether the distance between corresponding detected locations in the first and second sequences (i.e., detected locations appearing at corresponding positions in the first and second sequences) is decreasing or increasing, respectively, along the sequence.

As noted above, the touch-sensitive input device 120 and the display device 110 of the present embodiment are integrated in a touch-screen device 150. However, as also noted above, in other embodiments, the touch-sensitive input device 120 may be separate from the display device 110 and may, for example, be provided in the form of a track-pad that is provided as part of a computer keyboard or as a stand-alone peripheral component, although these examples are not exclusive.

The image manipulation module 130 is configured to determine, based on each of the touch interaction data 127 generated by touch-sensitive input device 120, a respective image manipulation that is to be performed on at least part of the image 200 being displayed by the display device 110. In other words, the image manipulation module 130 determines, from the touch interaction data, which type of manipulation is to be performed to at least part of the image 200. Each image manipulation may include, by example and without limitation, one or more of: (i) a resizing of both the foreground graphical planning element 210 and the background image 220 by a common scaling factor while maintaining the location of the foreground graphical planning element 210 with respect to the background image 220; (ii) a translation of the foreground graphical planning element 210 relative to the background image 220; and (iii) a panning of at least part of the image 200 being displayed, i.e., a panning of the foreground graphical planning element 210 and the background image 220 while maintaining the location of the foreground graphical planning element 210 with respect to the background image 220. The image manipulation module 130 is further configured to apply the determined image manipulation to the image 200 being displayed on the display device 110 in response to each of the touch interactions so as to generate a respective updated image that is displayed on the display device 110.

By way of example, where the plurality of touch interactions comprise a single-touch drag operation performed by the user on the touch-sensitive surface 125 of the input device 120, the touch-sensitive input device 120 generates touch interaction data 127 indicative of a sequence of detected locations for the single-touch drag, the sequence comprising a first detected location corresponding to a beginning of the single-touch drag and a second detected location corresponding to an end of the single-touch drag, as well as one or more intermediate detected locations that are between the first and second detected locations. The image manipulation module 130 may make use of a mapping to convert detected locations of a touch interaction on the touch-sensitive surface 125 to corresponding points on the background image 220 being displayed on the display device 110 during the touch interaction. In this case, where a location on the background image 220 corresponding to the first detected location (i.e., the location on the image 220 to which the first detected location is mapped) is within a predetermined distance from the foreground graphical planning element 210 (this distance being expressed in terms of any appropriate distance units defined in a coordinate system of the background image 220, from the first detected location in the sequence of detected locations to, e.g. a centre-of-mass, or the closest point on the boundary, of the foreground graphical planning element 210), the image manipulation module 130 is configured to determine the image manipulation for the single-touch drag to comprise a translation of the foreground graphical planning element 210 relative to the background image 220 by an amount that is based on a distance between the first and second detected locations and in a direction that is based on a direction of the second detected location from the first detected location. It should be noted that the predetermined distance may also be zero, in which case, for example, the first detected location is required to be on the external boundary of, or within, the foreground graphical planning element 210. For example, where the user touches the foreground graphical planning element 210 and moves their finger (or the stylus, as the case may be) across the touch-sensitive surface 125, the image manipulation module 130 determines the image manipulation to be a single-touch drag of the foreground graphical planning element 210, and accordingly determines the image manipulation for the single-touch drag to comprise a movement of the foreground graphical planning element 210 relative to the background image 220 by an amount that is based on a distance between the first and second detected locations and in a direction that is based on a direction of the second detected location from the first detected location.

Figure 4A:
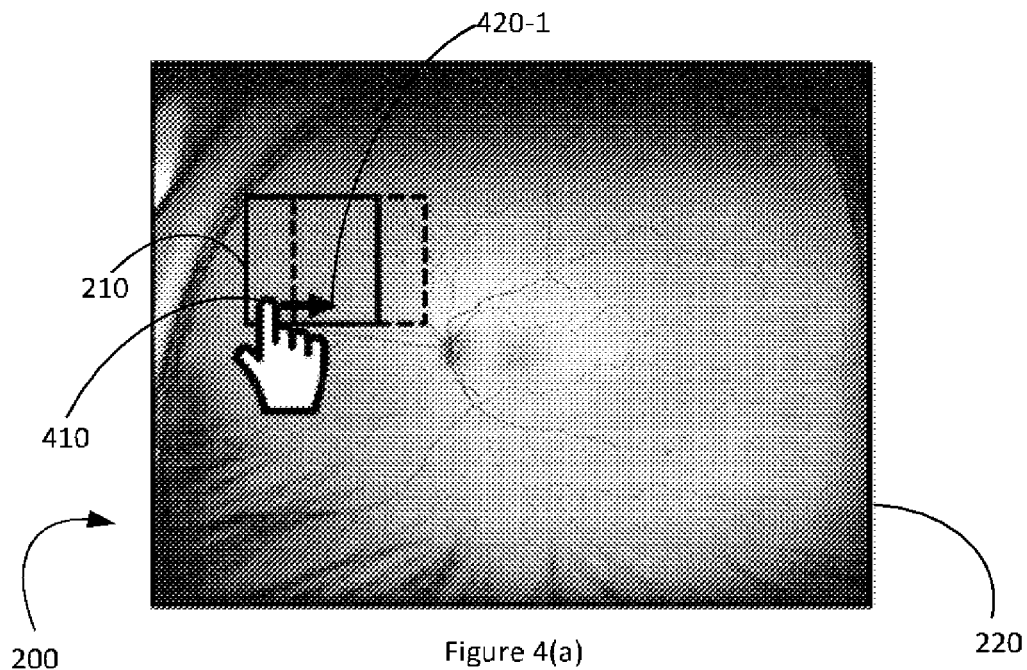
FIGS. 4(*a*) and 4(*b*) illustrate the updating of a displayed image to show a single-touch drag of the foreground graphical planning element in relation to the background image, according to an example aspect herein.
Figure 4B:
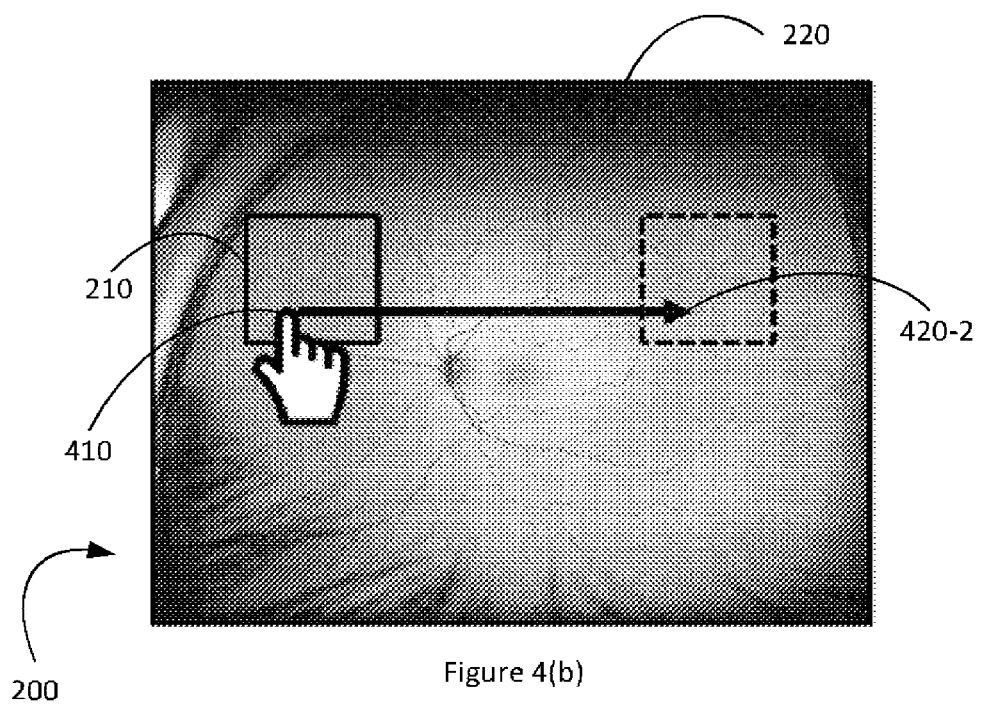

FIGS. 4(*a*) and 4(*b*) are illustrative examples of how the image manipulation module 130 may update the displayed image 200 in response to a touch interaction in the form of a single-touch drag operation performed by the user on the touch-sensitive surface 125 of a touch-sensitive input device 120 in the form of touch screen device, for example. The user touches the foreground graphical planning element 210 at a first touch location 410 on the touch screen device, and drags their digit (or stylus tip, as the case may be) horizontally across the surface of the touch screen device, to a second location, labelled 420-1 in FIG. 4(*a*) and 420-2 in FIG. 4(*b*). In an illustrated example embodiment herein, the image manipulation module 130 determines the touch interaction to be a single-touch drag, and that the (mapped) location on the background image 220 which corresponds to the first detected location is within the predetermined distance from the foreground graphical planning element 210, as described above. Accordingly, the module 130 updates the image 200 by translating the foreground graphical planning element 210 horizontally across the touch screen device, from an initial location (e.g., a location where the foreground graphical planning element is represented by a solid line in FIGS. 4(*a*) and 4(*b*)) to a final location (e.g., a location where the foreground graphical planning element is represented by a dashed line), by an amount of displacement corresponding to the distance between the first location 410 and the second location 420-1 or 420-2, whilst the background image 220 remains unchanged in the two images.

The image manipulation module 130 may more generally be configured to determine the image manipulation for the single-touch drag to comprise a translation of the foreground graphical planning element 210 relative to the background image 220 by an amount of displacement that scales linearly or non-linearly with the distance between the first and second detected locations and in a direction in the coordinate space represented on the display device 110 that is similar to, and preferably the same as, the direction of the second detected location from the first detected location on the touch-sensitive surface 125 of the touch-sensitive input device 120. The image manipulation module 130 may be configured to allow the user to adjust the linear or non-linear scaling between the translation amount and the distance between the first and second detected locations for the single-touch drag of the foreground graphical planning element 210, thereby effectively adjusting the sensitivity of the touch-sensitive input device 120 for the single-touch drag of the foreground graphical planning element 210. In other words, the user can specify the amount by which the element 210 is displaced (whether linearly or non-linearly) for each unit of the single-touch drag displacement, to thereby control/adjust the sensitivity. In other embodiments herein, the sensitivity is predetermined by pre-programming in the image manipulation module 130, or the user may specify a sensitivity or select a default sensitivity.

The image being displayed may be updated continually, for example at regular intervals, during the course of the single-touch drag, so that the value of the scan graphic locator is updated to change the location of the foreground graphical planning element 210 on the background image 220 effectively in real-time, while the user is performing the drag across the touch-sensitive input device 120). Also in one example embodiment herein, in response to the changing of the graphical planning element 210, the displayed image 200 is updated in a continuous manner, at predetermined intervals during the changing of the scan graphic locator in response to the single-touch drag, or after a predetermined delay. Alternatively, in another example embodiment, the image being displayed may be updated only after the single-touch drag operation has ended, i.e. after the user lifts their digit or stylus off the touch-sensitive input device 120. Which particular type of updating of the displayed image 200 is provided in response to the single-touch drag can be predetermined, or can be pre-specified/pre-programmed by user-command.

It should be noted that updating of the scan graphic locator to reflect the changing location of the point of contact of the user's digit/stylus in accordance with the aforementioned scaling (whether user-adjustable or not) may be conditional upon the scan graphic locator value being within a predetermined range of values bounded by predetermined bounds (e.g., a predetermined range of spatial coordinate values), and the predetermined range/bounds may be pre-programmed in the apparatus 100 or specified by user-command. In one example embodiment herein, the predetermined range/bounds are employed to ensure that the user cannot designate a region for the OCT scan where an OCT scan cannot in fact be performed for practical reasons. Thus, in one example, to the extent that the drag of graphical planning element 210 by the user causes the graphic locator value to exceed the bounds of the predetermined range, the graphic planning element 210 is no longer displaced and/or updated further beyond where the corresponding bound is reached by the scan graphic locator value. In one example embodiment herein, in the case where a value of the scan graphic locator is caused to exceed a predetermined bound of the range, in response to the drag by the user, then the scan graphic locator is maintained at a coordinate value corresponding to the predetermined bound, and the graphic planning element 120 is displayed at a position/orientation corresponding to that value of the scan graphic locator.

On the other hand, in a case of a single-touch drag where the location on the background image 220 corresponding to first detected location is not within the predetermined distance from the foreground graphical planning element 210 as described above, the image manipulation module 130 is configured to determine the image manipulation for the single-touch drag to comprise a panning of the image 200 being displayed (in other words, a common translation of both the background image 220 and the foreground graphical planning element 210, which preserves the location and orientation of the foreground graphical planning element 210 relative to the background image 220). In the present example embodiment, the amount of displacement resulting from the panning is based on the distance between the first and second detected locations, and the direction of the panning displacement is based on the direction of the second detected location from the first detected location. Thus, for example, in a case where the user touches the touch-sensitive surface 125 at a location thereon corresponding to a location in the background image 220 that is far enough away (i.e., not with the predetermined distance) from (or not on) the foreground graphical planning element 210, and moves their finger (or the stylus, as the case may be) across the touch-sensitive surface 125, the image manipulation module 130 determines the image manipulation to be a panning of the image 200, and accordingly determines that both the background image 220 and the foreground graphical planning element 210 are to be moved by an amount that is based on a distance between the first and second detected locations and in a direction based on that extending from the first detected location to the second detected location. In this case, the scan graphic locator maintains its position on the background image 220, both before and after the panning.

Figure 5:
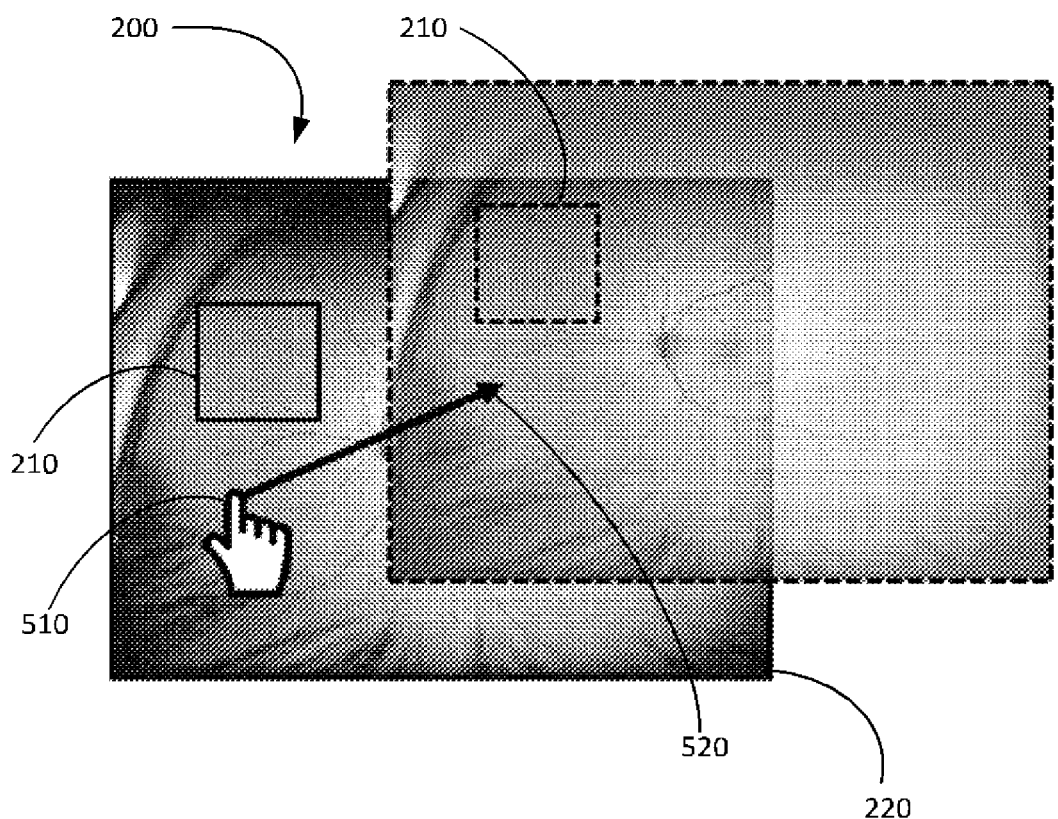
FIG. 5 illustrates the panning of a displayed image in response to a single-touch drag, whereby both the foreground graphical planning element and the background image move together, according to an example aspect herein.

FIG. 5 is an illustrative example of how the image manipulation module 130 may update the displayed image 200 in response to a touch interaction in the form of a single-touch drag operation performed by the user on the touch screen device, wherein the user does not touch the foreground graphical planning element 210, but instead places their digit or a tip of a stylus at a first touch location 510 on the touch screen device, wherein the first touch location 510 is detected as a first detected location. In the illustrated example, a location on the background image 220 corresponding to (i.e., mapped to) the first detected location is assumed to not be within a predetermined distance from the foreground graphical planning element 210, and the user drags the digit/stylus tip across the surface of the touch screen device, to a second location 520. The image manipulation module 130 determines the touch interaction to be a single-touch drag, and determines that the location on the background image 220 corresponding to the first detected location is not within the predetermined distance from the foreground graphical planning element 210, as described above, and accordingly updates the image 200 by translating both the foreground graphical planning element 210 and the background image 220 across the touch screen device by an amount corresponding to the distance between the first location 510 and the second location 520, and in a direction based on that extending from the first location 510 to the second location 520. In FIG. 5, the foreground graphical planning element 210 and a surrounded portion of the background image are bounded by a solid line, while the foreground graphical planning element 210 and the surrounded portion of the background image in the updated image are bounded by a dashed line.

The image manipulation module 130 may more generally determine the image manipulation for the panning operation to comprise a translation of both the foreground graphical planning element 210 and the background image 220 by an amount that scales linearly or non-linearly with the distance between the first and second detected locations, and in a direction on the display device 110 that is similar to, and preferably the same as, the direction of the second detected location from the first detected location on the touch-sensitive surface 125 of the touch-sensitive input device 120. The image manipulation module 130 may be configured to allow the user to adjust the linear or non-linear scaling between the translation amount and the distance between the first and second detected locations for the panning operation, thereby effectively adjusting the sensitivity of the touch-sensitive input device 120 for the panning operation. In other words, the user can specify the amount by which the element 210 and image 220 are displaced (whether linearly or non-linearly) for each unit of displacement along the (imaginary) line extending from the first detected location to the second detected location, to thereby control/adjust the sensitivity. In some embodiments herein, the sensitivity is predetermined by pre-programming in the image manipulation module 130, and the user can select between the pre-programmed sensitivity and a sensitivity specified by the user.

Where the plurality of touch interactions comprise a pinch operation performed by the user on the touch-sensitive surface 125 of the input device 120, the touch-sensitive input device 120 generates touch interaction data 127 indicative of a first sequence of detected locations and a second sequence of detected locations, as described above. In this case, the image manipulation module 130 may be configured to determine the image manipulation for the pinch to comprise a resizing of both the foreground graphical planning element 210 and the background image 220 by a common scaling factor which is based on a difference between (i) a distance between the first detected locations in the first and second sequences of detected locations, and (ii) a distance between the final detected locations in the first and second sequences of detected locations; in other words, a difference between the separation of the detected locations on the touch-sensitive surface 125 at the beginning of the pinch operation and the separation of the detected locations on the touch-sensitive surface 125 at the end of the pinch operation. The image manipulation module 130 may alternatively be configured to adjust the common scaling factor (and thus adjust the size of the element 210 and background image 220) based on a calculated distance from either of the two touch locations (i.e. the points of contact mentioned above) to a predetermined reference location, such as, by example and without limitation, a location that is equidistant from the initial touch locations of the pinch operation, when either of the touch locations are detected to change.

Figure 6A:
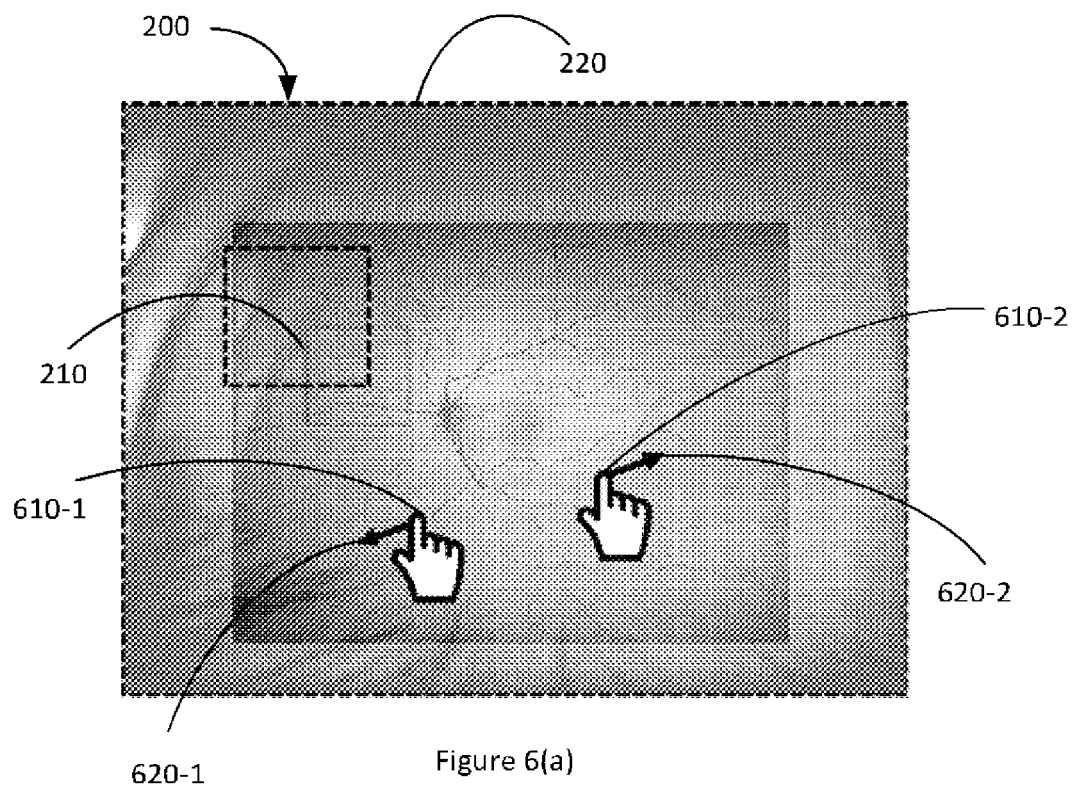
FIGS. 6(*a*) to 6(*c*) illustrate the zooming of a displayed image in response to a pinch operation, according to an example aspect herein.
Figure 6B:
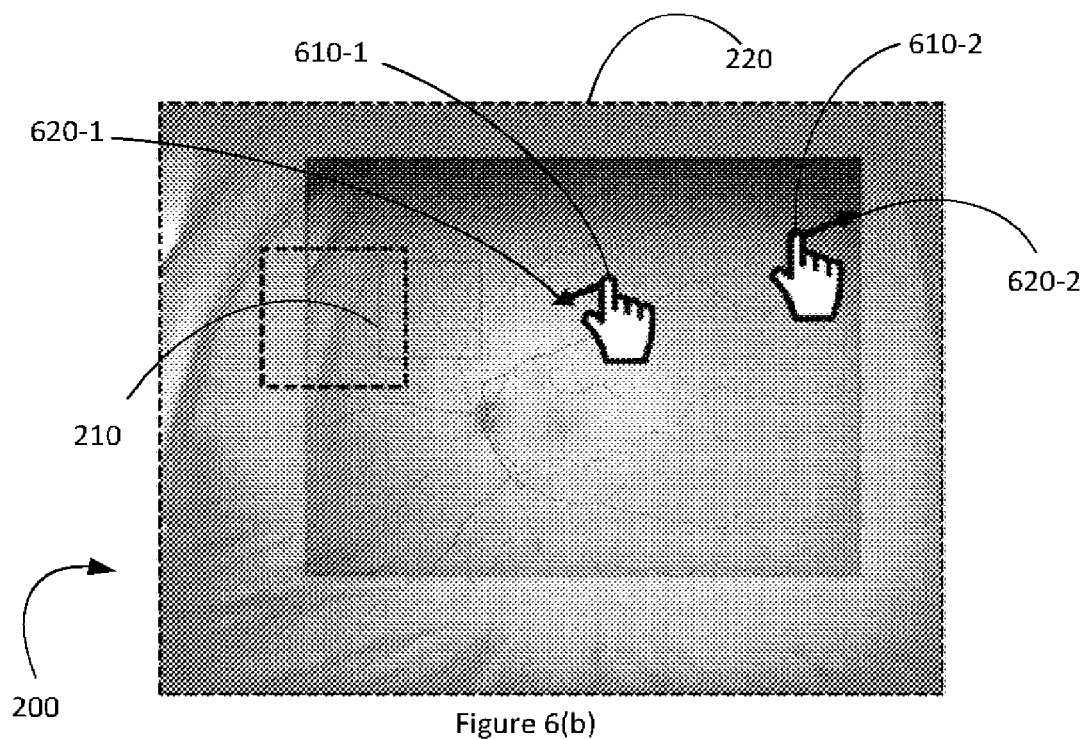
Figure 6C:
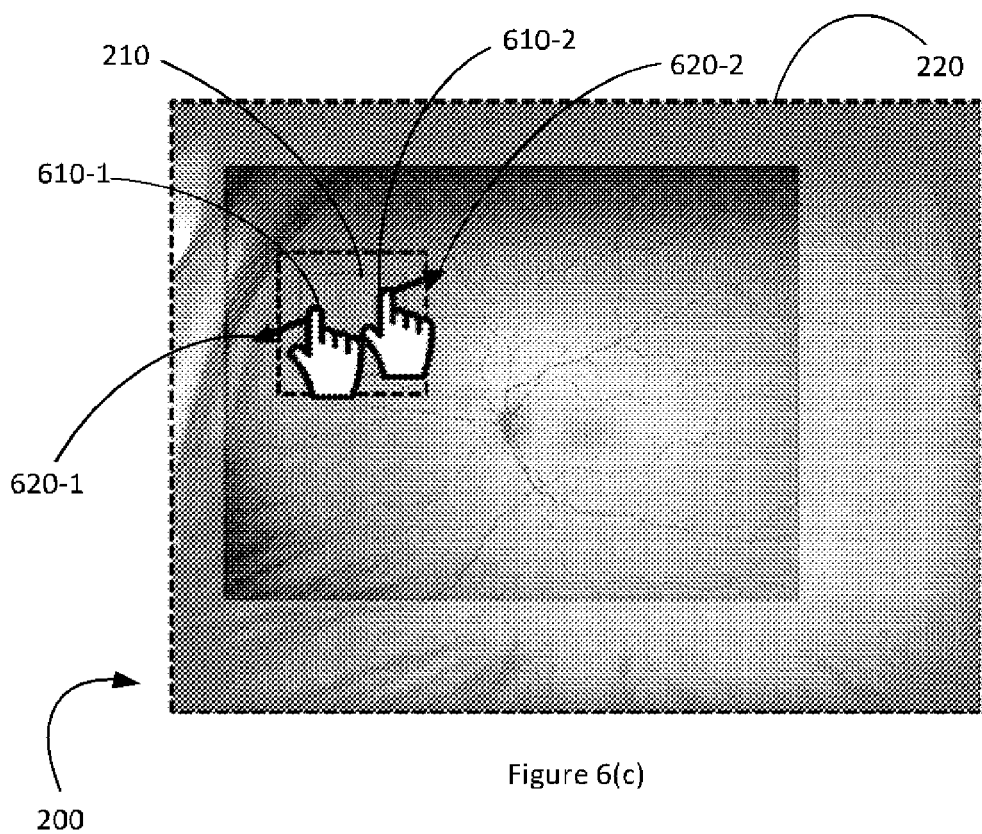

FIG. 6(a) is an illustrative example of how the image manipulation module 130 may update the displayed image 200 in response to a touch interaction in the form of a pinch operation performed by the user on the touch screen device, but where the user does not touch the foreground graphical planning element 210, and instead places their digits (typically the thumb and forefinger of a hand, although the pinch operation may more generally be performed using any two digits, and not necessarily those of a same hand) at respective first touch locations, 610-1 and 610-2, and drags the digits away from each other across the surface of the touch screen device, to respective second touch locations, 620-1 and 620-2. The image manipulation module 130 determines the touch interaction to be a pinch operation, and accordingly updates the image 200 by resizing both the foreground graphical planning element 210 and the background image 220 by a common scaling factor that may, as in the present example embodiment, be based on the difference between the separation of the detected locations 610-1 and 610-2, and/or the separation of the detected locations 620-1 and 620-2. In FIG. 6(a), the foreground graphical planning element 210 and a surrounded portion of the background image in the initially-displayed image are bounded by a solid line, while the foreground graphical planning element 210 and the portion of the background image in the updated image are bounded by a dashed line. In the case of the pinch operation, the updating of the displayed image is independent of the initial placement of the digits on the touch screen (or other touch-sensitive input device), i.e. at the start of the touch interaction, and depends only on the relative movement of the points of contact between the digits and the touch-sensitive surface 125 in the pinch operation. Thus, for example, where the relative movement of the points of contact between the digits and the touch-sensitive surface 125 is the same as those in the example of FIG. 6(a), but the locations of the initial points of contact of the digits with the touch-sensitive surface 125 are different than those in the example of FIG. 6(a), then the updated image will be the same, as illustrated in FIGS. 6(b) and 6(c). In other words, regardless of where the two initial points of contact of the digits with the touch-sensitive surface 125 are (i.e., both over the foreground graphical planning element 210, both over the background image 220, or one over the foreground graphical planning element 210 and the other over the background image 220), the image manipulation module 130 behaves in the same way, by updating the displayed image 200 such that the foreground graphical planning element 210 and the background image 220 zoom together, with the location and orientation of the foreground graphical planning element 210 with respect to the background image 220 being retained. As in the case of the single-touch drag, the image may be updated continually during the course of the pinch interaction, at predetermined intervals during the pinch interaction, after a predetermined delay, or after the operation has ended.

Figure 7A:
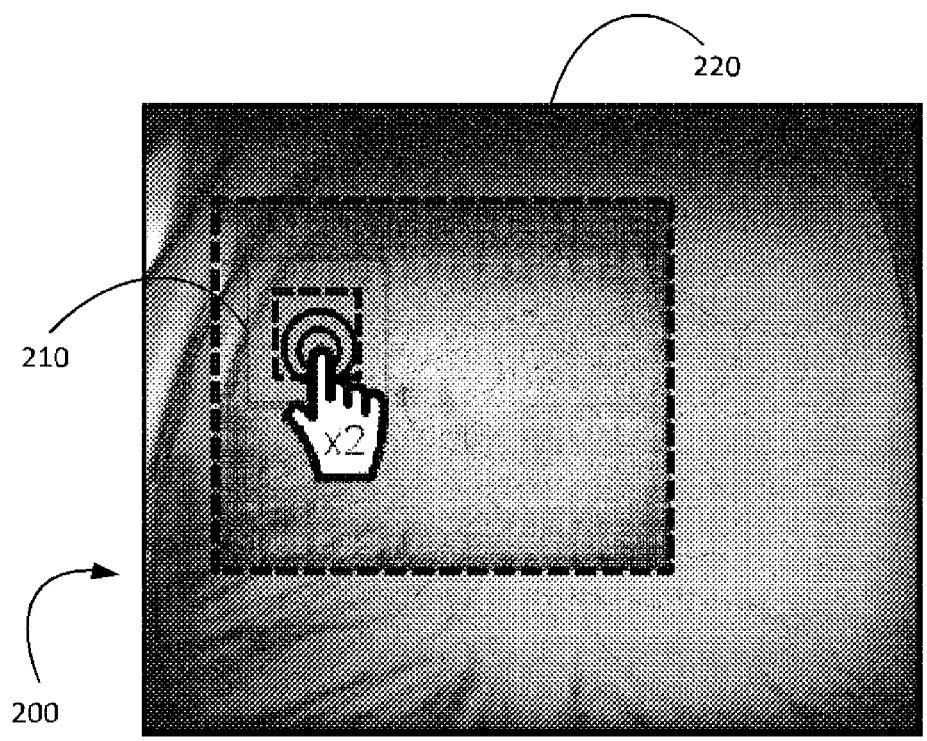
FIGS. 7(*a*) and 7(*b*) illustrate the zooming of a displayed image in response to a double-tap operation, according to an example aspect herein.
Figure 7B:
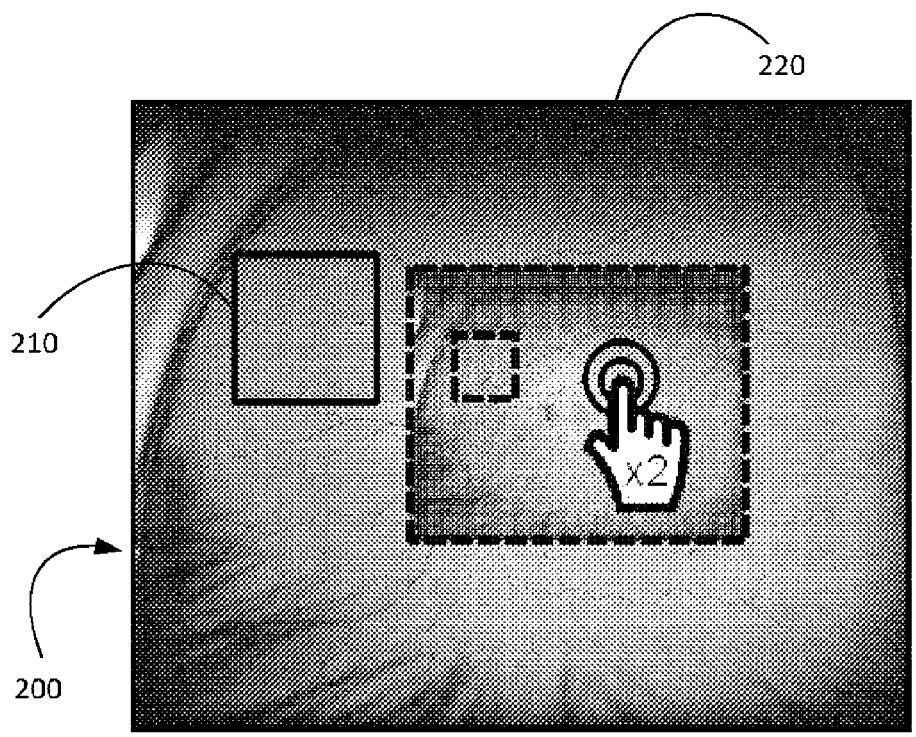

An example of a case where touch interactions include a double-tap operation will now be described. Where touch interactions comprise a double-tap operation performed by the user on the touch-sensitive surface 125 of the input device 120, the image manipulation module 130 is configured to determine the image manipulation for the double-tap operation to be a resizing of both the foreground graphical planning element 210 and the background image 220 by a common predetermined factor. The image manipulation module 130 may, as in the present embodiment, be configured to determine the image manipulation for the double-tap operation to be such that a portion of the image 200 provided at a location in the image 200 corresponding to a location of the double-tap on the touch-sensitive surface 125 appears at the same location in the updated image, allowing the image 200 (including both the background image 220 and the foreground graphical planning element 210) to be zoomed or visually expanded manner to enable closer examination of a region of interest in a quick and convenient way. As illustrated in FIGS. 7(a) and 7(b), the zooming/expanding is independent of whether the double-tap occurs over the foreground graphical planning element 210 (as illustrated in FIG. 7(a)), or over the background image 220 (this alternative being illustrated in FIG. 7(b)). Thus, regardless of where the points of contact on the touch-sensitive surface 125 occur in the double-tap operation (e.g., both over the foreground graphical planning element 210 or both over the background image 220), the image manipulation module 130 behaves on the same way, updating the displayed image 200 such that the foreground graphical planning element 210 and the background image 220 zoom/expand together, with the location and orientation of the foreground graphical planning element 210 with respect to the background image 220 being retained after the zoom/expansion.

The image manipulation module 130 may alternatively be configured to determine the image manipulation for the double-tap operation to comprise a translation of the image 200 being displayed, such that a portion of the image 200 provided at a location corresponding to a location of the double-tap on the touch-sensitive surface 125 appears at the centre of the updated image, for example. As a further alternative, the image manipulation module 130 may be configured to determine the image manipulation for the double-tap operation to be such that a portion of the image 200 provided at the centre of the image 200 also appears at a centre of the updated image.

In an alternative embodiment, the image manipulation module 130 may be configured to determine the image manipulation for a double-tap operation performed using a single finger to comprise a translation of the image 200 being displayed such that a portion of the image 200 provided at a location corresponding to a location of the double-tap on the touch-sensitive surface 125 appears at a centre of the updated image, and to determine the image manipulation for a double-tap operation performed using more than one finger to be such that a portion of the image 200 provided at the centre of the image 200 also appears at the centre of the updated image, thus combining the functionalities described above.

Although the double-tap operations are described to yield a zooming-in or expanding of the displayed image 200 in the foregoing examples, they may alternatively allow the user to zoom out of the currently displayed image 200. In this case, where the updated image fills the screen of the display device 110, the double-tap to zoom out would not cause the double-tap position to be retained. That is, a portion of the image 200 provided at a location in the image 200 corresponding to a location of the double-tap on the touch-sensitive surface 125 will not appear at the same location in the updated image, as described above.

It should be noted that at least some of the user interactions described above may be combined, with the image manipulation module 130 determining the image manipulation to comprise a combination of one or more of the image manipulations described above. For example, the image manipulation module 130 may track the coordinate of a mid-point of an imaginary line joining the first and second detected touch locations (contact points) during a pinch operation, and update the displayed image by panning it in accordance with the movement of the mid-point, whilst at the same time zooming the image in accordance with the changing distance between the first and second touch locations. Of course, this example is non-limiting and any other types of combinations of image manipulations also can be provided as well.

When a touch interaction event occurs on the background image 220 or the foreground graphical planning element 210, no action with respect to image 220 and/or element 210 may be performed until it is confirmed that the touch interaction event is not a double-tap. If it is confirmed that the touch interaction is not a double tap, no action with respect to the foreground graphical planning element 210 may be performed. Thus, the scan graphic locator may maintain the foreground graphical planning element 210's position on the background image 220 when, for example, panning or zooming due to a double-tap touch interaction event occurs. The proportionate distance of the position of the foreground graphical planning element 210 from the centre of the image 200 may be updated when either image manipulation event occurs. This distance may be calculated with respect to a reference position for each position change to prevent any "drifting" that would occur if the calculation was made from a relative position. The reference position may be set when the initial touch or double-tap is made on the background image 220, and, in one example embodiment, the reference position is the location of where the touch or double-tap is detected. Also in one example embodiment herein, the reference position can be reset if a touch up or touch leave event occurs.

Referring again to FIG. 1, the scan location designation module 140 will now be described. The scan location designation module 140 is configured to generate OCT scan location data 145 indicative of the location of the OCT scan that is to be performed on the retina based on a location of the foreground graphical planning element 210 on the background image 220 of the retina in at least one of the updated images, such as, for example, an updated image resulting from a most recent image manipulation comprising a translation of the foreground graphical planning element 210 relative to the background image 220, although this example is non-limiting.

The scan location designation module 140 may be configured to generate the OCT scan location data 145 on the basis of the location of the foreground graphical planning element 210 on the background image 220 in any suitable way. For example, the OCT scanner (not shown) may perform an OCT retinal scan covering an anatomical feature, such the fovea, that is generally recognisable in images of different modality, and generate data comprising OCT measurement values and corresponding scan parameter values that are indicative of, for example, the angular displacements of a first (e.g. horizontal) mirror and a second (e.g., vertical) mirror of the OCT scanner that are arranged to deflect the OCT sample beam across the surface of the retina. In an example embodiment involving such a case, the scan location designation module 140 may make use of the generated data and a mapping between locations in an obtained OCT retinal scan and corresponding locations in the background image 220 (which may be determined by comparing the locations of the fovea or any other recognisable anatomical feature(s) in the OCT retinal scan image and the background image 220) to calculate the scan parameter values corresponding to the location of the foreground graphical planning element 210 on the background image 220.

The location of the foreground graphical planning element 210 on the background image 220 may be defined in any suitable way. For example, where the foreground graphical planning element 210 takes the form of a rectangle, as illustrated in FIG. 2, the location of the foreground graphical planning element 210 may be taken to be the location of a geometrical centre (centre of mass) of the rectangle on the background image 220. Where the foreground graphical planning element 210 is a line segment, the location of the OCT scan indicated by OCT scan location data 145 may be based on a middle point or either end of the line segment, for example.

The scan location designation module 140 may, as in the present embodiment, be configured to generate OCT scan location data 145 that are indicative not only of the location of the OCT scan to be performed by the OCT scanner but also the size of that OCT scan, the size being based on at least one dimension of the foreground graphical planning element 210 in at least one of the updated images. For example, where the foreground graphical planning element 210 is a line segment for designating the location of a B-scan to be performed by the OCT scanner (not shown), whose length is adjustable by the user, the scan location designation module 140 may include in the generated scan location data, in addition to data indicative of the location of the OCT scan described above, data indicative of the length of the OCT scan, on the basis of the length of the line segment selected or otherwise set by the user. The width and/or height of a rectangular foreground graphical planning element 210 may likewise be adjustable by the user to allow the width and/or height of a rectangular OCT scan region to be set by the scan location designation module 140, in accordance with the user's requirements. The scan location designation module 140 may be configured to generate OCT scan location data 145 indicative of both the location and size of the OCT scan that is to be performed on the retina based on the location (on the background image 220) and the size of the foreground graphical planning element 210 in an updated image resulting from a most recent image manipulation comprising a translation of the foreground graphical planning element 210 relative to the background image 220 and a most recent manipulation comprising a resizing of the foreground graphical planning element 210.

The OCT scan location data 145 may be provided to an OCT scanner and used to control the OCT scanner to perform an OCT scan on the location on the retina indicated by the OCT scan location data 145.

In order to do so, the OCT scanner may be configured to transformed the location on the retina indicated by the OCT scan location data 145 into a corresponding set of one or more control parameters for steering the OCT scanner to perform its scan at substantially the same location on the retina as that indicated by the OCT scan location data 145. This can be done in one of a number of different ways.

For example, the OCT scanner may use a mapping between the locations on the retina and corresponding values of the control parameters, which may be provided in the form of a look-up table or a function defined by a set of parameters, for example. The mapping may be determined by calibration, using techniques known to those skilled in the art.

The apparatus 100 can thus allow the user to easily and conveniently explore all areas of the image 200 of a portion of the retina, varying the zoom level and/or panning across the image 200 as necessary, and moving the foreground graphical planning element 210 where needed during this exploration in order to designate a region of interest for the OCT scan. Accordingly, the apparatus 100 can allow an OCT scan to be planned anywhere on the background image 220, not merely in a magnified area of interest shown in a static background image as in conventional approaches.

Even in situations in which the user of the apparatus 100 is aware of an approximate intended location of the OCT scan (for example, in a case where the retina of the patient has been subject to an OCT scan previously), the features of the apparatus 100 allow the user to easily and conveniently explore the area around the approximate intended location of the OCT scan to determine whether there are further features of interest.

Second Embodiment

Figure 8:
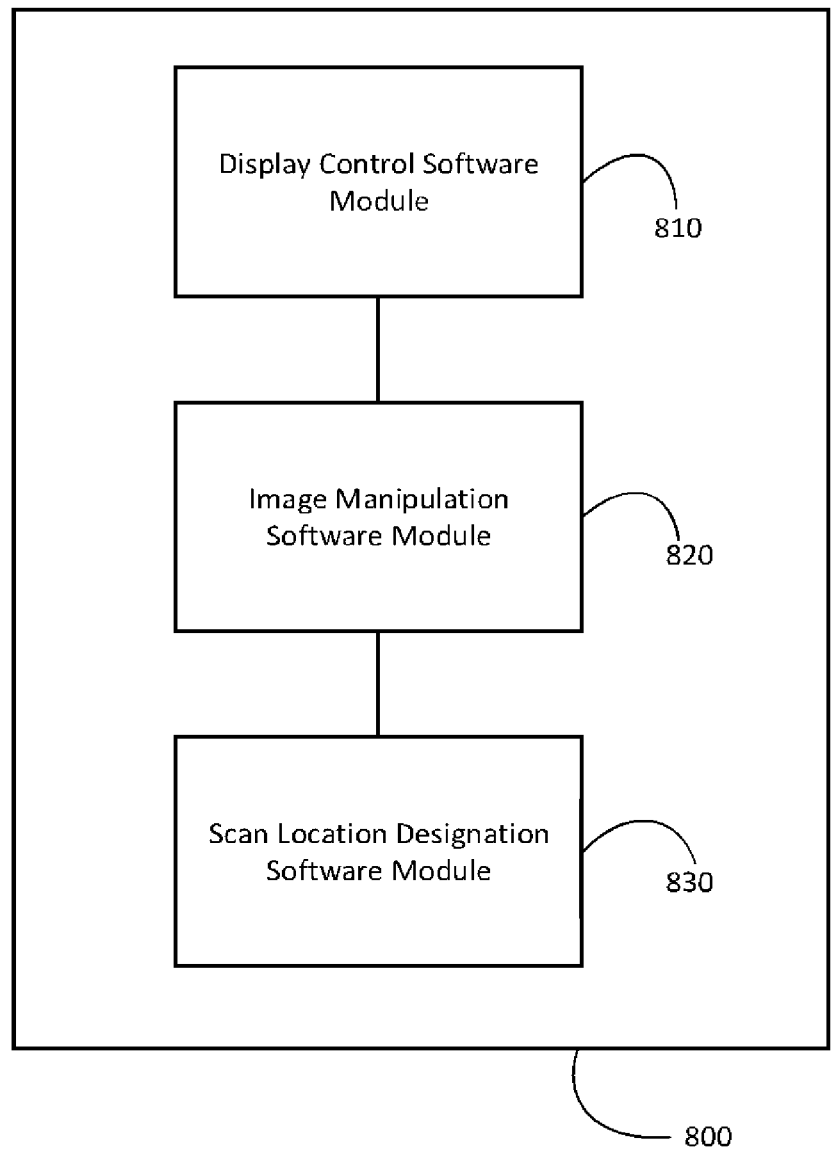
FIG. 8 is a schematic illustration of a computer program for designating a location of a retinal OCT scan, according to a second embodiment herein.
Figure 9:
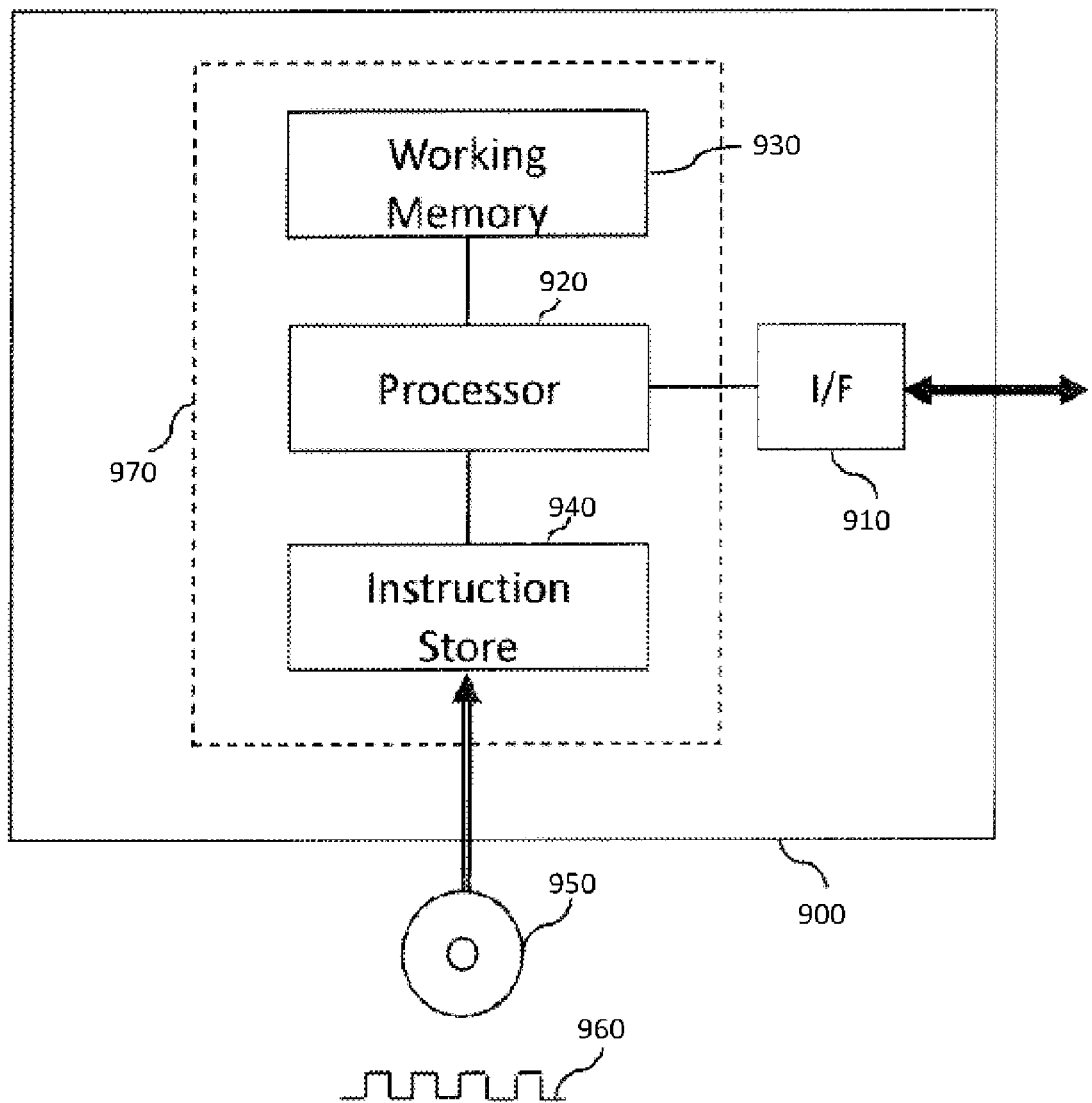
FIG. 9 is a block diagram illustrating an example of programmable signal processing hardware for executing the computer program of FIG. 8, according to the second example embodiment herein.

FIG. 8 illustrates a second example embodiment of the invention, provided in the form of a computer program 800 for designating a location of an OCT scan to be performed on a retina of an eye. The computer program 800 comprises a display control software module 810, an image manipulation software module 820, and a scan location designation software module 830. The computer program 800 comprises computer-readable instructions that may be executed by programmable signal processing hardware, an example of which is illustrated in FIG. 9. The computer-readable instructions may be executed by a computer processor, such as, by example, processor 920 of FIG. 9, to enable the processor 920 to perform any of the methods described herein.

The example of a programmable signal processing hardware 900 shown in FIG. 9 comprises a communication interface (I/F) 910 for receiving the touch interaction data 127 described above (e.g., from device 120), and outputting display control signals for controlling the display device 110 to display the image 200 and updated versions thereof, as also described above. The signal processing apparatus 900 further comprises processor (e.g., a Central Processing Unit, CPU, or Graphics Processing Unit, GPU) 920, a working memory 930 (e.g., a random access memory) and an instruction store 940 storing computer-readable instructions which, when executed by the processor 920, cause the processor 920 to perform various functions including those of the image manipulation module 130 and the scan location designation module 140 described above, as well as any method described herein. The instruction store 940 may store program 800 and may comprise a ROM (e.g., in the form of an electrically-erasable programmable read-only memory (EEPROM) or flash memory) which is pre-loaded with the computer-readable instructions. Alternatively, the instruction store 940 may comprise a RAM or similar type of memory, and the computer-readable instructions of the computer program 800 can be input thereto or otherwise received from computer program storage, such as a non-transitory, computer-readable storage medium 950 in the form of a CD-ROM, DVD-ROM, etc., or from a computer-readable signal 960 carrying the computer-readable instructions.

In the present embodiment, the combination 970 of the hardware components shown in FIG. 9, including the processor 920, the working memory 930 and the instruction store 940, is configured to perform the functions of the image manipulation module 130 and the scan location designation module 140 described above, and is configured to exchange information (including the touch interaction data and the display control signals) with the display device 110 and the touch-sensitive input device 120. It should be noted, however, that the image manipulation module 130 and the scan location designation module 140 may alternatively be implemented in non-programmable hardware, such as an application-specific integrated circuit (ASIC).

It will therefore be appreciated that the display control software module 810 shown in FIG. 8, when executed by the processor 920 illustrated in FIG. 9, causes the processor 920 to generate, based on image data defining the background image 220 and the foreground graphical planning element 210, display control signals for controlling a display device 110 to display the image 200 defined by the image data.

The image manipulation software module 820, when executed by the processor 920, causes the processor 920 to receive respective touch interaction data 127 indicative of at least one sequence of detected locations on a touch-sensitive surface 125 of the touch-sensitive input device 120 for each of a plurality of touch interactions of a user with the touch-sensitive surface 125, and determine, based on each of the touch interaction data 127, a respective image manipulation to be performed on the image data that define the image 200 being displayed by the display device 110 (each image manipulation comprising, as described above, e.g., at least one of: a resizing of both the foreground graphical planning element 210 and the background image 220 by a common factor; a translation of the foreground graphical planning element 210 relative to the background image 220; and a panning of the image 200 being displayed). The image manipulation software module 820, when executed by the processor 920, further causes the processor 920 to apply the determined image manipulation to the image data that define the image 200 being displayed by the display device 110, in response to each of the touch interactions, so as to generate a respective updated image data defining an updated image that is to be displayed on the display device 110, and causes the display control software module 810 to generate, based on the updated image data generated in response to each of the touch interactions, respective display control signals for controlling the display device 110 to display an updated image defined by the updated image data.

The scan location designation software module 830, when executed by the processor 920, causes the processor 920 to generate OCT scan location data 145 indicative of the location of the OCT scan that is to be performed on the retina based on a location of the foreground graphical planning element 210 on the background image 220 of the retina in at least one of the updated images.

Similar the first embodiment described above, where the plurality of touch interactions comprise a single-touch drag operation performed by the user on the touch-sensitive surface 125 of the input device 120 as described above, the image manipulation software module 820 may, when executed by the processor 920, make use of a mapping to convert detected locations of a touch interaction on the touch-sensitive surface 125 to corresponding points on the background image 220 being displayed on the display device 110 during the touch interaction(s). Similar to the first embodiment, where a location on the background image 220 corresponding to the first detected location is within the predetermined distance from the foreground graphical planning element 210, the image manipulation software module 820 causes the processor 920 to determine the image manipulation for the single-touch drag to comprise a translation of the foreground graphical planning element 210 relative to the background image 220 by an amount that is based on a distance between the first and second detected locations and in a direction that is based on a direction of the second detected location from the first detected location. It should be noted that the predetermined distance may also be zero, in which case the first detected location is required to be on the external boundary of, or within, the foreground graphical planning element 210. Thus, where the user touches the foreground graphical planning element 210 and moves their finger (or the stylus, as the case may be) across the touch-sensitive surface 125, the image manipulation software module 820 determines the image manipulation to be a single-touch drag of the foreground graphical planning element, and accordingly determines the image manipulation for the single-touch drag to comprise a movement of the foreground graphical planning element 210 relative to the background image 220 by a displacement amount that is based on a distance between the first and second detected locations and in a direction that is based on a direction of the second detected location from the first detected location.

For example, the image manipulation software module 820 may be configured to determine the image manipulation for the single-touch drag to comprise a translation of the foreground graphical planning element 210 relative to the background image 220 by an amount that scales linearly or non-linearly with the distance between the first and second detected locations and in a direction on the display device 110 that is the same as the direction of the second detected location from the first detected location on the touch-sensitive surface 125 of the touch-sensitive input device 120. The image manipulation software module 820 may cause the processor 920 to allow the user to adjust the linear or non-linear scaling between the translation amount and the distance between the first and second detected locations for the single-touch drag of the foreground graphical planning element 210, thereby effectively adjusting the sensitivity of the touch-sensitive input device 120 for the single-touch drag of the foreground graphical planning element 210.

On the other hand, in a case of a single-touch drag where the location on the background image 220 corresponding to first detected location is not within the predetermined distance from the foreground graphical planning element 210 as described above, the image manipulation software module 820, when executed by the processor 920, causes the processor 920 to determine the image manipulation for the single-touch drag to comprise a panning of the image 200 being displayed (in other words, a common translation of both the background image 220 and the foreground graphical planning element 210, which preserves the location of the foreground graphical planning element 210 relative to the background image 220) by an amount that is based on the distance between the first and second detected locations and in a direction that is based on the direction of the second detected location from the first detected location. Thus, where the user touches the touch-sensitive surface 125 at a location therein corresponding to a location in the background image 220 that is far enough away (e.g., not within the predetermined distance) from (or not on) the foreground graphical planning element 210 and moves their finger (or the stylus, as the case may be) across the touch-sensitive surface 125, the image manipulation software module 820 causes the processor 920 to determine the image manipulation to be a panning of the image 200, and accordingly to determine that both the background image 220 and the foreground graphical planning element 210 are to be moved by a displacement amount that is based on a distance between the first and second detected locations and in a direction that is based on a direction extending from the first detected location to the second detected location. For example, the image manipulation software module 820 may cause the processor 920 to determine the image manipulation for the panning operation to comprise a translation of both the foreground graphical planning element 210 and the background image 220 by an amount that scales linearly or non-linearly with the distance between the first and second detected locations, and in a direction on the display device 110 that is the same as the direction of the second detected location from the first detected location on the touch-sensitive surface 125 of the touch-sensitive input device 120. The image manipulation software module 820 may cause the processor 920 to allow the user to adjust the linear or non-linear scaling between the translation amount and the distance between the first and second detected locations for the panning operation, thereby effectively adjusting the sensitivity of the touch-sensitive input device 120 for the panning operation.

Where the plurality of touch interactions comprise a pinch operation performed by the user on the touch-sensitive surface 125 of the input device 120, the touch-sensitive input device 120 generates touch interaction data 127 indicative of a first sequence of detected locations and a second sequence of detected locations, as described above. In this case, the image manipulation software module 820 causes the processor 920 to determine the image manipulation for the pinch to comprise a resizing of both the foreground graphical planning element 210 and the background image 220 by a common scaling factor which is based on a difference between (i) a distance between the first detected locations in the first and second sequences of detected locations, and (ii) a distance between the final detected locations in the first and second sequences of detected locations; in other words, a difference between the separation of the detected first and second locations on the touch-sensitive surface 125 at the beginning of the pinch operation and the separation of the detected first and second locations on the touch-sensitive surface 125 at the end of the pinch operation.

Where the plurality of touch interactions comprise a double-tap operation performed by the user on the touch-sensitive surface 125 of the input device 120, the image manipulation software module 820 causes the processor 920 to determine the image manipulation for the double-tap operation to be a resizing of both the foreground graphical planning element 210 and the background image 220 by a common predetermined factor (e.g. a magnification by a factor of 2). The image manipulation software module 820 may, as in the present embodiment, cause the processor 920 to determine the image manipulation for the double-tap operation to be such that a portion of the image 200 provided at a location in the image 200 corresponding to a location of the double-tap on the touch-sensitive surface 125 appears at the same location in the updated image, allowing the image 200 (including both the background image 220 and the foreground graphical planning element 210) to be zoomed or visually expanded for closer examination of a region of interest in a quick and convenient way.

The image manipulation software module 820 may alternatively cause the processor 920 to determine the image manipulation for the double-tap operation to comprise a translation of the image 200 being displayed, such that a portion of the image 200 provided at a location corresponding to a location of the double-tap on the touch-sensitive surface 125 appears at a centre of the updated image. As a further alternative, the image manipulation software module 8200 may cause the processor 920 to determine the image manipulation for the double-tap operation to be such that a portion of the image 200 provided at the centre of the image 200 also appears at the centre of the updated image.

In an alternative embodiment, the image manipulation software module 820 may cause the processor 920 to determine the image manipulation for a double-tap operation performed using a single finger to comprise a translation of the image 200 being displayed such that a portion of the image 200 provided at a location corresponding to a location of the double-tap on the touch-sensitive surface 125 appears at the centre of the updated image, and to determine the image manipulation for a double-tap operation performed using more than one finger to be such that a portion of the image 200 provided at the centre of the image 200 also appears at the centre of the updated image, thus combining the functionalities described above.

Although the double-tap operations are described to yield a zooming-in (visual expanding) of the displayed image 200 in the foregoing, they may alternatively enable the user to zoom out of the currently displayed image 200. In this case, where the updated image fills the screen of the display device 110, the double-tap to zoom out does not cause the double-tap position to be retained, as described above.

The scan location designation software module 830 causes the processor 920 to generate OCT scan location data 145 indicative of the location of the OCT scan that is to be performed on the retina based on a location of the foreground graphical planning element 210 on the background image 220 of the retina in at least one of the updated images, such as, for example, an updated image resulting from a most recent image manipulation comprising a translation of the foreground graphical planning element 210 relative to the background image 220.

The scan location designation software module 830 may cause the processor 920 to generate the OCT scan location data 145 on the basis of the location of the foreground graphical planning element 210 on the background image 220 in any suitable way. For example, the OCT scanner may perform an OCT retinal scan covering an anatomical feature, such the fovea, that is generally recognisable in images of different modality, and generate data comprising OCT measurement values and corresponding scan parameter values that are indicative of, for example, the angular displacements of a first (e.g. horizontal) mirror and a second (e.g. vertical) mirror of the OCT scanner that are arranged to deflect the OCT sample beam across the surface of the retina; in this case, the scan location designation software module 830 may cause the processor 920 to make use of the generated data and a mapping between locations in the OCT retinal scan and corresponding locations in the background image 220 (which may be determined by comparing the locations of the fovea or any other recognisable anatomical feature(s) in the OCT retinal scan image and the background image 220) to calculate the scan parameter values corresponding to the location of the foreground graphical planning element 210 on the background image 220.

The location of the foreground graphical planning element 210 on the background image 220 may be defined in any suitable way, as described above with reference to the first embodiment.

The scan location designation software module 830 may, as in the present embodiment, cause the processor 520 to generate OCT scan location data 145 that are indicative not only of the location of the OCT scan to be performed by the OCT scanner (not shown) but also the size of that OCT scan, the size being based on at least one dimension of the foreground graphical planning element 210 in at least one of the updated images. For example, where the foreground graphical planning element 210 is a line segment for designating the location of a B-scan to be performed by the OCT scanner, whose length is adjustable by the user, the scan location designation software module 830 may include in the generated scan location data, in addition to data indicative of the location of the OCT scan described above, data indicative of the length of the OCT scan, on the basis of the length of the line segment selected or otherwise set by the user. The width and/or height of a rectangular foreground graphical planning element 210 may likewise be adjustable by the user to allow the width and/or height of a rectangular OCT scan region to be set by the scan location designation software module 830, in accordance with the user's requirements. The scan location designation software module 830 may cause the processor 920 to generate OCT scan location data 145 indicative of both the location and size of the OCT scan that is to be performed on the retina based on the location (on the background image 220) and the size of the foreground graphical planning element 210 in an updated image resulting from a most recent image manipulation comprising a translation of the foreground graphical planning element 210 relative to the background image 220 and a most recent manipulation comprising a resizing of the foreground graphical planning element 210.

Other details of the operations and their variants that are performed by the image manipulation module 130 and the scan location designation module 140 in the first embodiment are applicable to operations of the image manipulation software module 820 and the scan location designation software module 830, and will not be repeated here.

Figure 10:
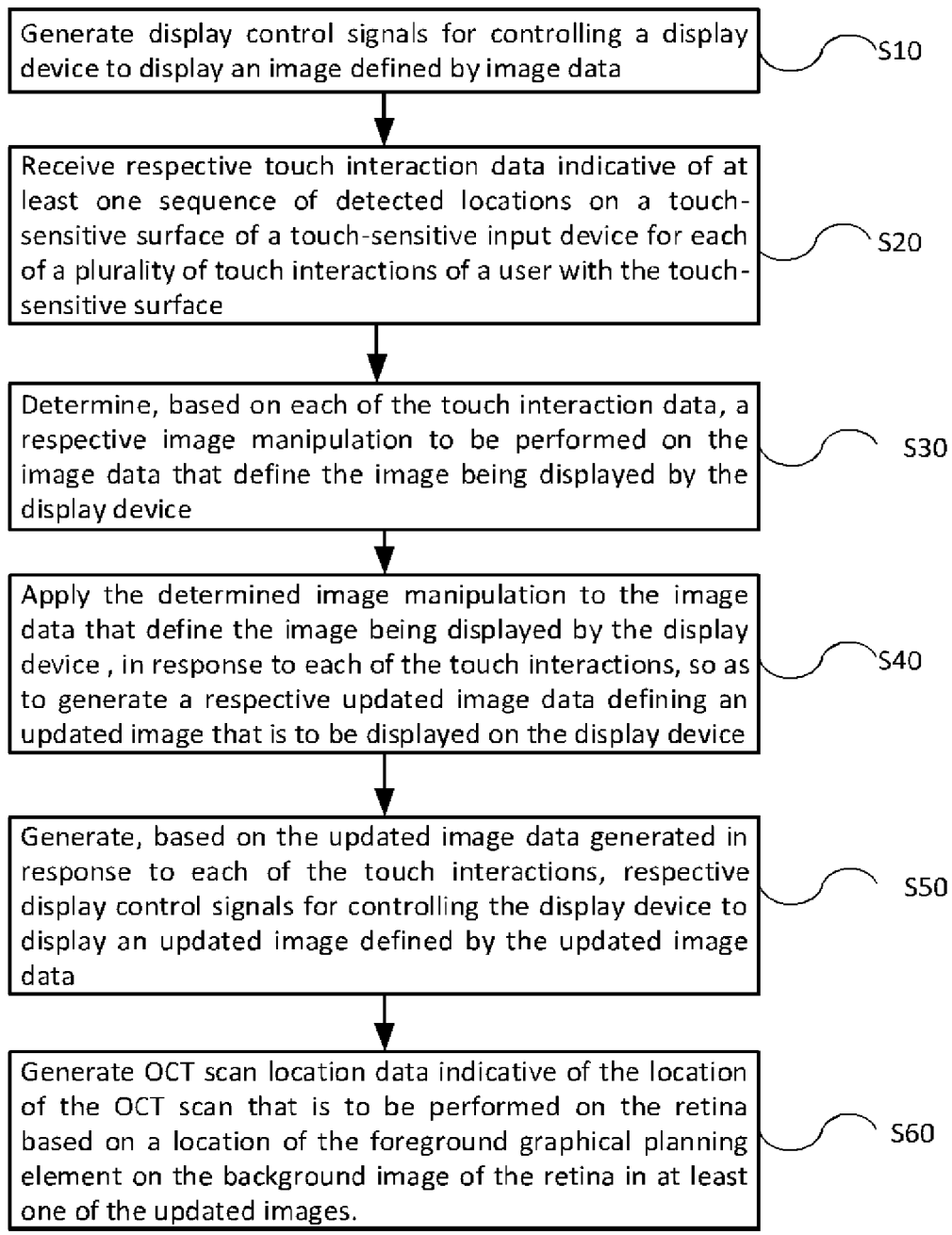
FIG. 10 is a flow diagram showing a process by which a computer program designates a location of an optical coherence tomography, OCT, scan to be performed on a retina of an eye, according to the second example embodiment herein.

It will be appreciated from the foregoing that the display control software module 810, the image manipulation software module 820 and the scan location designation module 830 may perform a method as shown in FIG. 10. FIG. 10 is a flow diagram showing a process 1000 by which the computer program 800 of FIG. 8 designates a location of an optical coherence tomography, OCT, scan to be performed on a retina of an eye.

In process S10 of FIG. 10, the display control software module 810 is executed by the processor 920 and causes the processor 920 to generate display control signals for controlling a display device 110 to display an image 200 defined by the image data. Generating the display control signals is based on image data defining a background image 220 of a portion of the retina and a foreground graphical planning element 210 for designating a location on the retina of the OCT scan to be performed.

In process S20, the image manipulation software module 820 is executed by the processor 920 and causes the processor 920 to receive respective touch interaction data 127 indicative of at least one sequence of detected locations on a touch-sensitive surface 125 of a touch-sensitive input device 120 for each of a plurality of touch interactions of a user with the touch-sensitive surface 125.

In process S30, the image manipulation software module 820 is executed by the processor 920 and causes the processor 920 to determine, based on each of the touch interaction data 127, a respective image manipulation to be performed on the image data that define the image 200 being displayed by the display device 110, each image manipulation comprising at least one of: a resizing of both the foreground graphical planning element 210 and the background image 220 by a common factor; a translation of the foreground graphical planning element 210 relative to the background image 220; and a panning of the image 200 being displayed.

In process S40, the image manipulation software module 820 is executed by the processor 920 and causes the processor 920 to apply the determined image manipulation to the image data that define the image 200 being displayed by the display device 110, in response to each of the touch interactions, so as to generate a respective updated image data defining an updated image that is to be displayed on the display device 110.

In process S50, the image manipulation software module 820 is executed by the processor 920 and causes the processor 920 to cause the display control software module 810 to generate, based on the updated image data generated in response to each of the touch interactions, respective display control signals for controlling the display device 110 to display an updated image defined by the updated image data.

In process S60, the scan location designation software module 830 is executed by the processor 920 and causes the processor 920 to generate OCT scan location data 145 indicative of the location of the OCT scan that is to be performed on the retina based on a location of the foreground graphical planning element 210 on the background image 220 of the retina in at least one of the updated images.

Other details of the operations and their variants that are performed by the computer program 800 of the second embodiment, as discussed above, are applicable to process 1000 of FIG. 10, and will not be repeated here.

It will be appreciated that the embodiments described above provide functionality that goes beyond simple panning and zooming of the image, allowing the coordinates, size and position of the foreground graphical planning element on the background image to be maintained, and the user to seamlessly interact with either the foreground graphical planning element or the combination of the foreground graphical planning element and the background image without any additional steps.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The apparatus and computer programs described herein may be embodied in other specific forms without departing from the characteristics thereof. The foregoing embodiments are illustrative rather than limiting of the described systems and methods. Scope of the apparatus and computer programs described herein is thus indicated by the appended claims, rather than the foregoing description, and changes that come within the meaning and range of equivalency of the claims are embraced therein.

The invention claimed is:

1. A non-transitory computer-readable storage medium storing instructions which, when executed by a computer processor, cause the computer processor to perform a method of designating a location of an optical coherence tomography (OCT) scan, by an OCT scanner, to be performed on a retina of an eye, the method comprising:
generating display control signals for controlling a display device to display one or more images, wherein generating of the display control signals is, based on image data defining a background image of a portion of the retina and a foreground graphical planning element for designating a location on the retina of the OCT scan to be performed;
receiving respective touch interaction data indicative of at least one sequence of detected locations on a touch-sensitive surface of a touch-sensitive input device for each of a plurality of touch interactions of a user with the touch-sensitive surface;
determining, based on each of the touch interaction data, one or more a respective image manipulations to be performed on image data defining at least one image currently being displayed by the display device, at least one of the image manipulations comprising at least one of:
a concurrent resizing of both the foreground graphical planning element and the background image by a common factor, while maintaining a location and orientation of the foreground graphical planning element with respect to the background image and without having moved the OCT scanner, wherein the concurrent resizing occurs in response to a touch interaction with the touch sensitive surface that selects only the background image, or
a panning of the image being displayed, the panning including commonly translating both the foreground graphical planning element and the background image while maintaining the location and orientation of the foreground graphical planning element with respect to the background image throughout the panning, wherein the panning is performed in response to a touch interaction with the touch sensitive surface that is outside of a predetermined distance from the foreground graphical planning element and which is the beginning of a drag operation;
applying the at least one image manipulation to the image data that define the image currently being displayed by the display device, so as to generate a respective updated image data defining an updated image that is to be displayed on the display device;
generating, based on the updated image data, at least one control signal for controlling the display device to display an updated image defined by the updated image data; and
generating OCT scan location data indicative of the location of the OCT scan that is to be performed on the retina based on a location of the foreground graphical planning element on the background image of the retina in at least one if the updated images.

2. The non-transitory computer-readable storage medium of claim 1, wherein:
at least one of the pluralities of touch interactions comprises a single-touch drag operation performed by the user on the touch-sensitive surface of the touch-sensitive input device;
the at least one sequence of detected locations for the single-touch drag comprises a first detected location corresponding to a beginning of the single-touch drag and a second detected location corresponding to an end of the single-touch drag; and
in a case where a touch interaction of the plurality of touch interactions is the single-touch drag and a location on the background image corresponding to the first detected location of the touch-sensitive surface is within the predetermined distance from the foreground graphical planning element, the method also comprises determining another image manipulation for the single-touch drag to comprise a translation of the foreground graphical planning element relative to the background image by an amount that is based on a distance between the first and second detected locations and in a direction that is based on a direction of the second detected location from the first detected location.

3. The non-transitory computer-readable storage medium of claim 1, wherein:
at least one of the plurality of touch interactions comprises a pinch operation performed by the user on the touch-sensitive surface of the touch-sensitive input device;
the at least one sequence of detected locations for the pinch operation comprises a first sequence of detected locations and a second sequence of detected locations; and
in a case of the pinch operation, the method also comprises determining another image manipulation for the pinch operation to comprises resizing of both the foreground graphical planning element and the background image by a common factor which is based on a difference between a distance between first detected locations in the first and second sequence of detected locations and a distance between final detected locations in the first and second sequences of detected locations.

4. The non-transitory computer-readable storage medium of claim 1, wherein:
at least one of the plurality of touch interactions comprises a double-tap operation performed by the user on the touch-sensitive surface of the touch-sensitive input device; and
in a case of the double-tap operation, the method also comprises determining a further image manipulation for the double-tap operation to comprise resizing of both the foreground graphical planning element and the background image by a common predetermined factor.

5. The non-transitory computer-readable storage medium of claim 4, wherein, in the case of the double-tap operation, the further image manipulation is determine such that:
a portion of the image at a location of the double-tap in the image currently being displayed appears at the same location in the updated image;
a portion at a location of the double-tap in the image currently being displayed appears at a center of the updated image; or
a portion of the image provided at a center of the display device appears at a center of the updated image.

6. The non-transitory computer-readable storage medium of claim 1, wherein the foreground graphical planning element comprises one of a point, a line segment, a rectangle and an ellipse.

7. The non-transitory computer-readable storage medium of claim 1, wherein the method further comprises generating, as part of the OCT scan location data, data defining a size of the OCT scan that is to be performed on the retina, based on at least one dimension of the foreground graphical planning element in at least one of the updated images.

8. An apparatus for designating a location of an optical coherence tomography (OCT) scan, by an OCT scanner, to be performed on a retina of an eye, the apparatus comprising:
- a display device configured to display an image comprising a background image of a portion of the retina and a foreground graphical planning element for designating a location on the retina of the OCT scan to be performed;
- a touch-sensitive input device having a touch-sensitive surface and configured to generate respective touch interaction data indicative of at least one sequence of detected locations for each of a plurality of touch interactions of a user with the touch-sensitive surface;
- an image manipulation module configured to:
  - determine, based on each of the touch interaction data, one or more image manipulations to be performed on at least one image currently being displayed by the display device, at least one of the image manipulations comprising at least one of:
    - a concurrent resizing of both the foreground graphical planning element and the background image by a common factor, while maintaining a location and orientation of the foreground graphical planning element with respect to the background image and without having moved the OCT scanner, wherein the concurrent resizing occurs in response to a touch interaction with the touch sensitive surface that selects only the background image, or
    - a panning of the image being displayed, the panning including commonly translating both the foreground graphical planning element and the background image, while maintaining the location and orientation of the foreground graphical planning element with respect to the background image throughout the panning, wherein the panning is performed in response to a touch interaction with the touch sensitive surface that is outside of a predetermined distance from the foreground graphical planning element and which is the beginning of a drag operation; and
  - apply the at least one image manipulation to the image currently being displayed on the display device so as to generate a respective updated image that is to be displayed on the display device; and
- a scan location designation module configured to generate OCT scan location data indicative of the location of the OCT scan that is to be performed on the retina based on a location of the foreground graphical planning element on the background image of the retina in at least one of the updated images,
- wherein each of the image manipulation module and the scan location designation module comprises hardware of a combination of hardware and software.

9. The apparatus of claim 8, wherein:
- at least one of the plurality of touch interactions comprises a single-touch drag operation performed by the user on the touch-sensitive surface of the input device;
- the at least one sequence of detected locations for the single-touch drag comprises a first detected location corresponding to a beginning of the single-touch drag and a second detected location corresponding to an end of the single-touch drag; and
- in a case where a touch interaction of the plurality of touch interactions is the single-touch drag and a location on the background image corresponding to the first detected location on the touch-sensitive surface is within the predetermined distance from the foreground graphical planning element, the image manipulation module is configured to also determine another image manipulations for the single-touch drag to comprise a translation of the foreground graphical planning element relative to the background image by an amount that is based on a distance between the first and second detected locations and in a direction that is based on a direction of the second detected location from the first detected locations.

10. The apparatus of claim 8, wherein:
- at least one of the plurality of touch interactions comprises a pinch operation performed by the user on the touch-sensitive surface of the input device;
- the at lease one sequence of detected locations for the pinch operation comprises a first sequence of detected locations and a second sequence of detected locations; and
- in a case of the pinch operation, the image manipulation module also is configured to determine another image manipulation for the pinch operation to comprise a resizing of both the foreground graphical planning element and the background image by a common factor which is based on a difference between a distance between first detected locations in the first and second sequences of detected locations and a distance between final detected locations in the first and second sequences of detected locations.

11. The apparatus of claim 8, wherein:
- at least one of the plurality of touch interactions comprises a double-tap operation performed by the user on the touch-sensitive surface of the input device; and
- in a case of the double-tap operation, the image manipulation module also is configured to determine a further image manipulation for the double-tap operation to comprise a resizing of both the foreground graphical planning elements and the background image by a common predetermined factor.

12. The apparatus of claim 11, where, in the case of the double-tap operation, the image manipulation is further configured to determine the further image manipulation such that a portion of the image at a location of the double-tap in the image being displayed appears at a same location in the updated image.

13. The apparatus of claim 11, where, in a case of the double-tap operation, the image manipulation module is further configured to determine the image manipulation for the double-tap operation to comprise a translation of the image currently being displayed such that a portion at a location of the double-tap in the image currently being displayed appears at a center of the updated image.

14. The apparatus of claim 11, where, in a case of the double-tap operation, the image manipulation module is further configured to determine the image manipulation for the double-tap operation to comprise a translation of the image currently being displayed such that a portion of the image provided at a center of the display device appears at a center of the updated image.

15. The apparatus of claim 8, wherein the foreground graphical planning element comprises one of a point, a line segment, a rectangle or an ellipse.

16. The apparatus of claim 8, wherein the display device and the touch-sensitive input device are included in a touch-screen screen.

17. The apparatus of claim 8, wherein the input device is a track-pad.

18. The apparatus of claim 8, wherein the scan location designation module is further configured to generate, as part of the OCT scan location data, data defining a size of the OCT scan that is to be performed on the retina, based on at least one dimension of the foreground graphical planning element in at least on of the updated images.

19. An apparatus for designating a location of an optical coherence tomography (OCT) scan, by an OCT scanner, to be performed on a retina of an eye, the apparatus comprising:

a display device configured to display an image comprising a background image of a portion of the retina and a foreground graphical planning element for designating a location on the retina of the OCT scan to be performed;

a touch-sensitive input device having a touch-sensitive surface and configured to generate respective touch interaction data indicative of at least one sequence of detected locations for each of a plurality of touch interactions of a user with the touch-sensitive surface;

a computer processor and a computer-readable storage medium storing instructions, wherein the instructions, when executed by the computer processor, cause the computer processor to:

determine, based on each of the touch interaction data, one or more image manipulations to be performed on at least one image currently being displayed by the display device, at least one of the image manipulations comprising at least one of:
         a concurrent resizing of both the foreground graphical planning element and the background image by a common factor, while maintaining a location and orientation of the foreground graphical planning element with respect to the background image and without having moved the OCT scanner, wherein the concurrent resizing occurs in response to a touch interaction with the touch sensitive surface that selects only the background image, or
         a planning of the image being displayed, the panning including commonly translating both the foreground graphical planning element and the background image while maintaining the location and orientation of the foreground graphical planning element with respect to the background image throughout the panning, wherein the panning is performed in response to a touch interaction with the touch sensitive surface that is outside of a predetermined distance from the foreground graphical planning element and which is the beginning of a drag operation;

apply the at least one image manipulation to the image currently being displayed on the display device so as to generate a respective updated image that is to be displayed on the display device; and generate OCT scan location data indicative of the location of the OCT scan that is to be performed on the retina based on a location of the foreground graphical planning element on the background image of the retina in at least one of the updated images.

20. A method of designating a location of an optical coherence tomography (OCT) scan, by an OCT scanner, to be performed on a retina of an eye, the method comprising:

generating display control signals for controlling a display device to display one or more images, wherein generating of the display control signals is, based on image data defining a background image of a portion of the retina and a foreground graphical planning element for designating a location on the retina of the OCT scan to be performed;

receiving respectful touch interaction data indicative of at least one sequence of detected locations on a touch-sensitive surface of a touch-sensitive input device for each of a plurality of touch interactions of a user with the touch-sensitive surface;

determining, based on each of the touch interaction data, one or more image manipulations to be performed on image data defining at least one image currently being displayed by the display device, at least one of the image manipulations comprising at least one of:
      a concurrent resizing of both the foreground graphical planning element and the background image by a common factor, while maintaining a location and orientation of the foreground graphical planning element with respect to the background image and without having moved the OCT scanner, wherein the resizing occurs in response to a touch interaction with the touch sensitive surface that selects only the background image, or
      a panning of the image being displayed, the panning including commonly translating both the foreground graphical planning element and the background image while maintaining the location and orientation of the foreground graphical planning element with respect to the background image throughout the panning, wherein the panning is performed in response to a touch interaction with the touch sensitive surface that is outside of a predetermined distance from the foreground graphical planning element and which is the beginning of a drag operation;

applying the at least one image manipulation to the image data that define the image currently being displayed by the display device, so as to generate a respective updated image data defining an updated image that is to be displayed on the display device;

generating, based on the updated image data, at least on control signal for controlling the display device to display an updated image defined by the updated image data; and generating OCT scan location data indicative of the location of the OCT scan that is to be performed on the retina based on a location of the foreground graphical planning element on the background image of the retina in at least one of the updated images.

* * * * *